United States Patent
Chi et al.

(10) Patent No.: US 12,281,331 B2
(45) Date of Patent: Apr. 22, 2025

(54) SEPARATION, DISSOCIATION AND/OR DISAGGREGATION OF CELLS USING SHOCKWAVES OR MECHANICAL IMPACTS

(71) Applicant: Synova Life Sciences, Inc., Pasadena, CA (US)

(72) Inventors: John Chi, Pasadena, CA (US); Ben-Chen Chi, Pasadena, CA (US)

(73) Assignee: Synova Life Sciences, Inc., Pasadena, CA (US)

( * ) Notice: Subject to any disclaimer, the term of this patent is extended or adjusted under 35 U.S.C. 154(b) by 0 days.

(21) Appl. No.: 18/507,966

(22) Filed: Nov. 13, 2023

(65) Prior Publication Data
US 2024/0076622 A1    Mar. 7, 2024

Related U.S. Application Data

(63) Continuation of application No. 16/085,200, filed as application No. PCT/US2017/023084 on Mar. 17, 2017, now Pat. No. 11,866,732.
(Continued)

(51) Int. Cl.
C12M 1/33    (2006.01)
C12N 5/0775   (2010.01)

(52) U.S. Cl.
CPC .......... *C12N 5/0667* (2013.01); *C12M 45/02* (2013.01); *C12N 2509/10* (2013.01)

(58) Field of Classification Search
CPC .............................. C12M 45/02; C12M 45/09
See application file for complete search history.

(56) References Cited

U.S. PATENT DOCUMENTS

| 5,728,130 A | 3/1998 | Ishikawa et al. |
| 6,890,728 B2 | 5/2005 | Doleck et al. |
| (Continued) | | |

FOREIGN PATENT DOCUMENTS

| CN | 2687654 | 3/2005 |
| CN | 1630526 | 6/2005 |
| (Continued) | | |

OTHER PUBLICATIONS

"Agitador vortex modelo Vortex MS3 Basic, marca IKA," (with English translation) Zelian Equipamiento De Laboratorio, Date Last Modified Apr. 15, 2021, retrieved from https://www.zelian.com.ar/detalle.php?articulo=EQL-01516&titulo=agitador-vortex-modelo-vortex-ms3-basic-marca-ika, 10 pages.
(Continued)

*Primary Examiner* — Jonathan M Hurst
(74) *Attorney, Agent, or Firm* — Sheridan Ross PC

(57) ABSTRACT

Methods provided by the present disclosure utilize extracorporeal shockwaves, mechanical impacts and/or principles of lithotripsy to break up a tissue sample into smaller fragments—clusters of cells and/or single cells—after which a desired cellular fraction can be isolated from the sample. Devices provided by the present disclosure deploy focused and/or directed shockwaves, and/or focused and directed mechanical impacts, to break apart a tissue sample. The devices maintain the sample in a sterile, closed environment during exposure to the shockwaves or mechanical impacts. Therefore, the shockwaves and/or mechanical impacts are generated outside of a closed device and are transmitted through one or more walls of the device into its interior, where the sample is located.

20 Claims, 5 Drawing Sheets

Related U.S. Application Data

(60) Provisional application No. 62/309,774, filed on Mar. 17, 2016.

(56) References Cited

U.S. PATENT DOCUMENTS

| | | |
|---|---|---|
| 7,018,354 B2 | 3/2006 | Tazi |
| 7,077,559 B2 | 7/2006 | Hlavinka et al. |
| 10,329,533 B2 | 6/2019 | Chi et al. |
| 10,668,105 B2 | 6/2020 | Harman et al. |
| 11,866,732 B2 | 1/2024 | Chi et al. |
| 2005/0025755 A1 | 2/2005 | Hedrick et al. |
| 2005/0095228 A1 | 5/2005 | Fraser et al. |
| 2005/0132775 A1 | 6/2005 | Laugharn et al. |
| 2005/0256077 A1 | 11/2005 | Henning |
| 2006/0051865 A1 | 3/2006 | Higgins et al. |
| 2008/0009885 A1 | 1/2008 | Del Giglio |
| 2008/0014181 A1 | 1/2008 | Ariff et al. |
| 2008/0186802 A1 | 8/2008 | Bungay et al. |
| 2009/0169642 A1 | 7/2009 | Fradette et al. |
| 2009/0304644 A1 | 12/2009 | Hedrick et al. |
| 2010/0112696 A1 | 5/2010 | Min |
| 2010/0152880 A1 | 6/2010 | Boyden et al. |
| 2011/0034832 A1 | 2/2011 | Cioanta et al. |
| 2012/0100611 A1 | 4/2012 | Kensy et al. |
| 2012/0164113 A1 | 6/2012 | Victor et al. |
| 2012/0195862 A1 | 8/2012 | Daley et al. |
| 2013/0034524 A1 | 2/2013 | Adha-Mohammadi |
| 2013/0344589 A1 | 12/2013 | Winkler et al. |
| 2014/0017783 A1 | 1/2014 | Gimble et al. |
| 2015/0093809 A1 | 4/2015 | Alt et al. |
| 2015/0218506 A1 | 8/2015 | Nash et al. |
| 2015/0231244 A1 | 8/2015 | Chi et al. |
| 2015/0353891 A1 | 12/2015 | Peterson et al. |
| 2016/0024450 A1 | 1/2016 | Quick et al. |

FOREIGN PATENT DOCUMENTS

| | | |
|---|---|---|
| CN | 1842589 | 6/2005 |
| CN | 102311941 | 1/2012 |
| CN | 102433299 | 5/2012 |
| CN | 102458302 | 5/2012 |
| CN | 103203043 | 7/2013 |
| CN | 103263440 | 8/2013 |
| CN | 203200258 | 9/2013 |
| CN | 103402646 | 11/2013 |
| CN | 103443272 | 12/2013 |
| CN | 103484365 | 1/2014 |
| CN | 103842496 | 6/2014 |
| CN | 104704111 | 6/2015 |
| CN | 204752692 | 11/2015 |
| CN | 106834121 | 6/2017 |
| CO | 08134632 | 3/2010 |
| DE | 102015109148 | 5/2016 |
| JP | S61-230957 | 10/1986 |
| JP | 2005-218376 | 8/2005 |
| JP | 2016-028614 | 3/2016 |
| KR | 10-2009-000784 | 1/2009 |
| WO | WO 2007/139551 | 12/2007 |
| WO | WO 2013/086199 | 6/2013 |
| WO | WO 2014/000031 | 1/2014 |
| WO | WO 2017/161343 | 9/2017 |

OTHER PUBLICATIONS

Burden, "Guide to the Disruption of Biological Samples—2012," Random Primers, No. 12, Jan. 2012, 25 pages.

Condé-Green et al., "Shift toward Mechanical Isolation of Adipose-derived Stromal Vascular Fraction: Review of Upcoming Techniques," PRS Global Open, vol. 4, No. 9, Sep. 1, 2016, 9 pages.

Raposio et al., "A Novel and Effective Strategy for the Isolation of Adipose-Derived Stem Cells: Minimally Manipulated Adipose-Derived Stem Cells for More Rapid and Safe Stem Cell Therapy," Plastic Reconstructive Surgery, vol. 133, No. 6, Jun. 30, 2014, pp. 1406-1409.

Official Action for U.S. Appl. No. 14/626,634, dated Jul. 26, 2017, 7 pages.

Official Action for U.S. Appl. No. 14/626,634, dated Jan. 19, 2018, 7 pages.

Official Action for U.S. Appl. No. 14/626,634, dated Apr. 11, 2018, 8 pages.

Notice of Allowance for U.S. Appl. No. 14/626,634, dated Feb. 8, 2019, 8 pages.

Supplemental Notice of Allowance for U.S. Appl. No. 14/626,634, dated Apr. 11, 2019, 2 pages.

Official Action for U.S. Appl. No. 16/085,200, dated Jul. 13, 2020, 8 pages. Restriction Requirement.

Official Action for U.S. Appl. No. 16/085,200, dated Jan. 12, 2021, 9 pages.

Official Action for U.S. Appl. No. 16/085,200, dated Jun. 23, 2021, 10 pages.

Official Action for U.S. Appl. No. 16/085,200, dated Dec. 22, 2022, 10 pages.

Official Action for U.S. Appl. No. 16/085,200, dated Jul. 13, 2022, 10 pages.

Official Action for U.S. Appl. No. 16/085,200, dated Feb. 24, 2023, 12 pages.

Notice of Allowance for U.S. Appl. No. 16/085,200, dated Oct. 31, 2023, 10 pages.

Goldberg, "Chapter 1: Mechanical/Physical Methods of Cell Disruption and Tissue Homogenization," in Methods in Molecular Biology, 2D Page: Sample Preparation and Fractionation (ed. Posch), vol. 424, Jan. 1, 2008, pp. 3-22.

Gray et al., "Development of a Novel Digestion Chamber for Human and Porcine Islet Isolation," Transplantation Proceedings, vol. 36, No. 4, May 1, 2004, pp. 1135-1138.

SEPARATION, DISSOCIATION AND/OR DISAGGREGATION OF CELLS USING SHOCKWAVES OR MECHANICAL IMPACTS

CROSS-REFERENCE TO RELATED APPLICATIONS

This application is a continuation of U.S. patent application Ser. No. 16/085,200, filed on Sep. 14, 2018; which is a 371 filing of International PCT Patent Application No. PCT/US2017/023084, filed Mar. 17, 2017; which claims the benefit of U.S. Provisional Patent Application No. 62/309,774, filed Mar. 17, 2016; the disclosures of each of which are incorporated herein by reference.

BACKGROUND

Cellular bioprocessing is a form of biopharmaceutical manufacturing, the goal of which is to establish reproducible and robust manufacturing processes for the isolation and/or production of therapeutic cells.

Current cellular manufacturing processes are highly user dependent, requiring human intervention at numerous points. Because of that dependence, current processes are tedious, highly variable, expensive, and produce low yields.

By way of example, many current manufacturing processes occur as follows: a tissue sample (lipoaspirate, whole blood, bone marrow, cord blood, etc.) is obtained from a patient. The obtained biological sample is transferred to laboratory for bio-processing. At the laboratory, a cell separation technique is employed in order to obtain a desired cell fraction. The cell fraction is then isolated and either transferred back to the point-of-care facility for patient use, or processed further by introduction into a bioreactor for cellular expansion. Some known methods of cell separation include the use of mechanical separation via ultrasonic cavitation, enzymatic digestion, or other mechanical means that involve contacting the sample with foreign objects (e.g., beads) in order to obtain a desired cell fraction. The use of enzymes results in an increased regulatory compliance burden, as enzymes must come into direct contact with the sample in order to produce the desired outcome. Enzymes can also damage the integrity of the cells harvested and potentially change their properties. The use of high-powered sonication is similarly flawed. The sonicator tip is fixed in frequency and must be introduced into the cell or tissue suspension, which has the potential to negatively impact sterility. Additionally, the use of such high energy sound waves introduces a large amount of energy into the sample, which manifests as heat. This can damage the cells, which reduces the yield of useable cells.

Once obtained, the expanded cellular product is then moved from the bioreactor where it is purified and concentrated. Test samples are removed from the washed and concentrated cell product for quality testing and, if the test results show an acceptable product, the final engineered cellular product is either prepared for long term storage, cryopreservation, administered to the patient from whom the sample was derived, or some combination of the foregoing.

As can be appreciated, several of these steps require moving the sample from one container to another, requiring heavy user intervention, which not only increases the risks of mislabeling or mishandling the sample or samples during processing, but also potentially negatively impacts the sterility, identity, purity or potency of the sample. Additionally, the time required to process a sample in this manner means that the desired cell fraction is not ready for delivery to the patient for hours, if not days, which may have a negative impact on the health of a patient. The potential for compromised sterility and the unreasonably long periods of time required to process cellular samples are unacceptable for patients, particularly those who are immunocompromised or who require immediate care, and are also unacceptable to providers, who need to provide timely, high-quality care for many patients.

SUMMARY

Thus, an optimized and scalable method of obtaining a desired cellular fraction in a short period of time directly at the point-of-care, and without the need for multiple user intervention, is needed. Devices capable of practicing that method are also needed. Such methods and devices are provided by the present disclosure. The disclosed methods and devices eliminate the need to transfer cellular samples to a laboratory for processing and do not contact the cellular sample with foreign objects during separation, resulting in a processed sample that provides a desired cellular sample in a very short period of time, with fewer user contacts, thereby allowing optimization of expensive technical resources.

The devices and methods disclosed herein have several features, no single one of which is solely responsible for its desirable attributes. Without limiting the scope of the claims that follow, certain features of the disclosed devices and methods will be discussed briefly. After considering this discussion, and particularly after reading the section entitled "Detailed Description" a person having ordinary skill in the art will understand how the features of the devices and methods provide several advantages over traditional systems and methods.

In one aspect, the present disclosure provides completely closed systems suitable for bio-processing of cellular samples, for example fat tissue samples that are processed for autologous stem cell therapy. The systems are not open to the air, thus allowing for sterile sample processing and transfer of the sample throughout the entirety of bio-processing.

In a first aspect, methods of isolating a cellular fraction from a tissue sample are provided, the methods comprising: obtaining a tissue sample from a subject; contacting the tissue sample with shock waves, force from mechanical impacts, or both; and isolating a cellular fraction from the tissue sample; wherein the source of the shock waves and/or the force from mechanical impacts does not make physical contact with the tissue sample.

In some embodiments, the tissue is selected from adipose tissue, brain tissue, pharyngeal tissue, laryngeal tissue, heart tissue, arterial tissue, muscle tissue, liver tissue, gall bladder tissue, kidney tissue, small intestinal tissue, large intestinal tissue, lymph node tissue, lung tissue, spleen tissue, bone marrow tissue, stomach tissue, venous tissue, pancreatic tissue, urinary bladder tissue, bone, teeth, dentin tissue, gum tissue, skin tissue, pineal gland tissue, pituitary gland tissue, thyroid gland tissue, adrenal gland tissue, pancreatic tissue, ovarian tissue and testicular tissue.

In some embodiments, the tissue is adipose tissue.

In some embodiments, the tissue sample is contacted with shock waves and the source of the shock waves is a shockwave applicator that is powered by a shockwave generator.

In some embodiments, the tissue sample is contacted with force from mechanical impacts and the source of the force from the mechanical impacts is an impact arm that is powered by a motor.

In some embodiments, the tissue sample is washed one or more times prior to contact with the shock waves and/or the force from the mechanical impacts.

In some embodiments, the shock waves break the tissue sample into a plurality of small clusters of cells, a plurality of individual cells, or both.

In some embodiments, the force from the mechanical impacts breaks the tissue sample into a plurality of small clusters of cells, a plurality of individual cells, or both.

In some embodiments, the cellular fraction comprises the plurality of small clusters of cells, plurality of individual cells, or both, and isolation of the cellular fraction occurs by centrifugation.

In some embodiments, centrifugation occurs for 3 to 30 minutes at a speed of 500 g to 2,000 g.

In some embodiments, centrifugation occurs for 10 minutes at 1,200 g.

In some embodiments, the isolated cellular fraction is resuspended after centrifugation.

In some embodiments, the cellular fraction is isolated in 30 minutes or less.

In a second aspect, methods of isolating stem cells from adipose tissue are provided, the methods comprising: obtaining an adipose tissue sample from a subject; placing the tissue sample into a container or cartridge; subjecting the tissue sample to force from mechanical impacts to release the stem cells; separating a stem cell fraction from the adipose tissue; and centrifuging the stem cell fraction; wherein the source of the force of the mechanical impacts does not physically contact the adipose tissue.

In some embodiments, the adipose tissue is washed one or more times prior to being subjected to the force from the mechanical impacts.

In some embodiments, the source of the force of the mechanical impacts is an impact arm that is powered by a motor, the motor comprising gearing capable of reducing the speed of the impact arm when the motor is operating at full speed.

In some embodiments, the force from the mechanical impacts is delivered to the adipose tissue through a wall of the container or cartridge.

In some embodiments, the gearing allows for a 10 to 1 reduction in speed in the impact arm.

In some embodiments, the motor comprises a gear diameter of 0.75 inches and at a motor speed of 3,000 rpm the impact arm has a speed of 117.8 inches per second.

In some embodiments, separating a stem cell fraction comprises allowing the adipose tissue to separate from an aqueous layer, the aqueous layer comprising the stem cells.

In some embodiments, the stem cells are isolated from the adipose tissue in 30 minutes or less.

In some embodiments, centrifugation occurs at 500 g to 1,600 g for 3 to 10 minutes.

In a third aspect, methods of isolating stem cells from adipose tissue are provided, the methods comprising: obtaining an adipose tissue sample from a subject; placing the tissue sample into a container or cartridge; subjecting the tissue sample to shock waves to release the stem cells; separating a stem cell fraction from the adipose tissue; and centrifuging the stem cell fraction; wherein the source of the shock waves does not physically contact the adipose tissue.

In some embodiments, the adipose tissue is washed one or more times prior to being subjected to the shock waves.

In some embodiments, the source of the shock waves is a shockwave applicator that is powered by a shockwave generator.

In some embodiments, the shockwaves are delivered to the adipose tissue through the wall of the container or cartridge.

In some embodiments, the adipose tissue is subjected to shock waves having a power of 0.5 to 5.0 bars.

In some embodiments, the container is a vinyl bag having walls that are 0.25 mm thick and the adipose tissue is subjected to shock waves having a power of 2.0 to 2.5 bars.

In some embodiments, the total area of the adipose tissue subjected to the shock waves at any one point in time ranges from 1 $cm^2$ to 100 $cm^2$.

In some embodiments, wherein the container is a 19 oz. vinyl bag having walls 0.25 mm thick, the total amount of the adipose tissue sample is 30 cc, and the total area of the adipose tissue subjected to the shock waves at any one point in time is 5 $cm^2$.

In some embodiments, the adipose tissue is subjected to a number of shock waves ranging from 5,000 to 100,000.

In some embodiments, separating a stem cell fraction comprises allowing the adipose tissue to separate from an aqueous layer, the aqueous layer comprising the stem cells.

In some embodiments, centrifugation occurs at 500 g to 1,600 g for 3 to 10 minutes.

DESCRIPTION OF THE DRAWINGS

The features and advantages of the present disclosure may be further explained by reference to the following detailed description and accompanying drawings that set forth illustrative embodiments.

DETAILED DESCRIPTION

Figure 1:
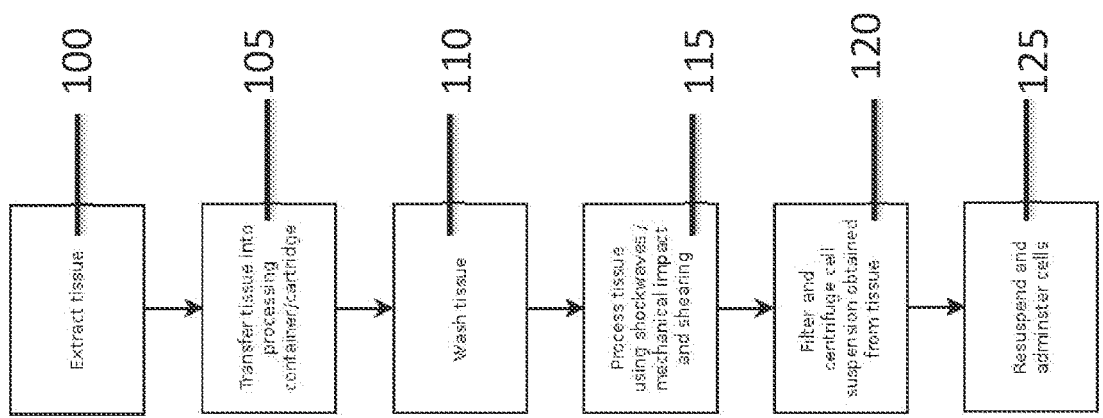
FIG. 1 provides an overview of a method of isolating a cellular fraction from a tissue sample, according to embodiments provided by the present disclosure.

Before the embodiments of the disclosure are described, it is to be understood that such embodiments are provided by way of example only, and that various alternatives to the embodiments of the disclosure described herein may be employed in practicing the disclosure. Numerous variations, changes, and substitutions will now occur to those skilled in the art without departing from the disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. In case of conflict, the patent specification, including definitions, will control. In addition, the materials, methods, and examples are illustrative only and not intended to be limiting. Numerous variations, changes, and substitutions will occur to those skilled in the art without departing from the disclosure.

As used in the specification and claims, the singular forms "a", "an" and "the" include plural references unless the context clearly dictates otherwise. For example, the term "a cell" includes a plurality of cells, including mixtures thereof.

As used herein, "extracorporeal shockwave," extracorporeal shockwaves" and/or "ESW" means abrupt, high amplitude pulses of mechanical energy, similar to soundwaves, that are generated externally to a sample of interest and then transmitted to that sample. In that respect, the generating source of the ESW does not make physical contact with the sample; the shockwaves themselves contact the sample, but the generating source does not. The extracorporeal shockwaves are thus generated by a source at some distance from the sample and are then transmitted to the sample. Transmission may occur through the air and/or through the wall of a container in which the sample is located. The ESW may be focused and/or directed, in order to, for example, concentrate the ESW in an area of interest that may cover the entire sample, or only a portion of it.

As used herein, "subject" or "patient" refers to a mammal, for example, a human.

Methods provided by the present disclosure utilize extracorporeal shockwaves, mechanical impacts, vibrations and/or principles of lithotripsy to break up a tissue sample into smaller fragments—clusters of cells and/or single cells—after which a desired cellular fraction can be isolated from the sample. In various aspects, the methods comprise isolating a sample from a subject, the sample comprising a cell type of interest, contacting that sample with extracorporeal shockwaves, but not the device used to generate the ESW, to break the sample into small clusters of cells and/or individual cells, and then isolating the cell type of interest from the broken sample.

Devices provided by the present disclosure utilize focused and/or directed shockwaves, and/or focused and directed mechanical impacts to break apart a sample of interest. In various aspects, the devices provided by the present disclosure maintain the sample in a sterile, closed environment during exposure to the shockwaves or mechanical impacts. Therefore, the shockwaves and/or mechanical impacts are generated outside of the closed, sterile container and are transmitted through one or more walls of the container into its interior, where the sample is located.

By maintaining the source of the ESW at a distance from the sample of interest, the source of the ESW (the device that generates them) does not make physical contact with the sample. This greatly improves the sterility of the sample and any cellular fraction that is isolated from the sample. From the point of view of a health care provider, this also greatly improves the requirements for sterility and helps ensure that the cellular fraction of interest derived from the sample is sterile for patient use. Additionally, maintaining the ESW generating source from the sample of interest ensures that the generator will not add energy or heat into the sample of interest, which can damage or kill cells, damage DNA and dramatically decrease the yield. In that respect, the devices provided by the present disclosure are an improvement to other, known systems such as ultrasound.

The methods and devices provided by the present disclosure are capable of isolating a desired cellular fraction from a tissue sample quickly, in some embodiments in 30 minutes or less. The speed at which the disclosed methods and devices may be used imparts a significant advantage in that the desired cellular fraction that is isolated from the sample can be available for use immediately.

Methods

FIG. 1 presents a method of isolating a cellular fraction of interest from a tissue sample, according to embodiments provided by the present disclosure.

In the depicted embodiment, the method begins by first extracting tissue from a subject (100). The tissue can be of any type, provided that the tissue will break down when subjected to extracorporeal shockwaves. In some embodiments, the tissue is adipose tissue, or fat. In some embodiments, the tissue is from an internal organ, for example the brain, pharynx, larynx, heart, arteries, muscle, liver, gall bladder, kidney, small intestine, large intestine, lymph nodes, lungs, spleen, bone marrow, stomach, veins, pancreas, urinary bladder, bone, teeth, dentin, gum or skin. In some embodiments the tissue is from a component of the endocrine system, for example the pineal gland, pituitary gland, thyroid gland, adrenal gland, pancreas, ovary or testis.

Extraction can occur via any number of known methods. In some embodiments, tissue extraction occurs via a syringe. In some embodiments, tissue extraction occurs surgically such that the tissue sample is placed into a first container upon removal from the subject.

The tissue is then transferred into a processing container or cartridge 105. Devices provided by the present disclosure provide all of the components required for fast and easy-to-use ESW cellular bio-processing. Even though some of the components of the disclosed methods and/or devices are separable from each other, they are configured to connect to each other in a completely sterile manner, thereby allowing transfer of the sample from one component to another during processing. In that respect, the entirety of the sample is processed in a single system, thereby ensuring sterility.

The sterile transfer is performed without exposing the sample to the outside environment. In that respect, the transfer can occur via any number of ways that will maintain the closed, sterile environment. In some embodiments, the transfer is accomplished by attaching male and female luer lock connectors to each other between the first container, which contains the sample extracted from the subject, and the processing container or cartridge. In some embodiments, the transfer is accomplished by sterile-docking the first container and the processing container or cartridge using a sterile connection device. The sample is transferred, either mechanically or by gravity flow, from the first container to the processing container or cartridge.

In some embodiments, the first container is inserted into the cartridge and sterile-docked using a sterile connection device to become the processing container within the cartridge. The first container as the processing chamber already contains the sample.

In that respect, in this disclosure each time a tissue and/or cellular sample is disclosed as being moved from one container to another, such movement can occur so as to maintain the integrity of the closed system, thereby not exposing the sample to the outside environment.

Once the sample is transferred to the processing container or cartridge, the tissue sample is washed one or more times 110. The washing can occur as described herein, via the use of sterile saline solution. Washing ensures that the sample is devoid of as many impurities as possible before processing, thus increasing the purity level of the cellular fraction to be isolated therefrom.

In some embodiments, washing is performed by mechanical agitation of the processing container or cartridge. If multiple washing steps are desired and/or necessary, the sterile saline is drained from the processing container or cartridge after a single wash is complete, and new sterile saline introduced into the container or cartridge for each subsequent wash. In that respect, each time the sterile saline is drained and new sterile saline is introduced into the container or cartridge, it is done so as to maintain the closed, sterile environment, as described herein.

After washing, the tissue sample is processed 115. As indicated, processing can occur via the use of ESW, mechanical impact, vibration and shearing, or combinations thereof.

In some embodiments, processing occurs via ESW and the tissue sample is broken down into a plurality of small clusters of cells. In some embodiments, processing occurs via ESW and the tissue sample is broken down into a plurality of small clusters of cells and a plurality of individual cells. In some embodiments, processing occurs via ESW and the tissue sample is completely broken down into a plurality of individual cells.

In some embodiments, processing occurs via mechanical impact and shearing and the tissue sample is broken down into a plurality of small clusters of cells. In some embodiments, processing occurs via mechanical impact and shearing and the tissue sample is broken down into a plurality of small clusters of cells and a plurality of individual cells. In some embodiments, processing occurs via mechanical impact and shearing and the tissue sample is completely broken down into a plurality of individual cells.

In some embodiments, processing occurs via a combination of ESW and mechanical impact and shearing and the tissue sample is broken down into a plurality of small clusters of cells. In some embodiments, processing occurs via a combination of ESW and mechanical impact and shearing and the tissue sample is broken down into a plurality of small clusters of cells and a plurality of individual cells. In some embodiments, processing occurs via a combination of ESW and mechanical impact and shearing and the tissue sample is completely broken down into a plurality of individual cells.

After processing, the cell suspension representing what is left of the sample, which may be a plurality of small clusters of cells, a plurality of individual cells, or both, is filtered and centrifuged 120. Filtering can occur either in a device separate from the processing container or cartridge, or within the processing container or cartridge itself. In some embodiments, filtering occurs in a separate device, in which case the cell suspension is transferred to the filter via sterile means, as described herein. In some embodiments, filtering occurs as the cell suspension is being moved from the container or cartridge into one or more centrifuge tubes.

In some embodiments, transfer to the filtering device is accomplished by attaching male and female luer lock connectors to each other between the processing container or cartridge and the filtering device. In some embodiments, the transfer is accomplished by sterile-docking the processing container or cartridge and the filtering device using a sterile connection device. The sample is transferred, either mechanically or by gravity flow, from the processing container or cartridge to the filtering device.

In some embodiments, filtering occurs within the processing container or cartridge, as described herein.

In various aspects, centrifugation occurs outside of the processing container or cartridge. In some embodiments, the cell suspension is transferred to one or more centrifuge tubes located inside of the processing container or cartridge. When filled, the centrifuge tubes are moved from the processing container or cartridge to a centrifuge via sterile means, as described herein.

In some embodiments, the cell suspension is transferred to one or more centrifuge tubes located outside of the processing container or cartridge via sterile means, as described herein. When filled, the centrifuge tubes are moved from the processing container or cartridge to a centrifuge via sterile means, as described herein.

The duration and speed of centrifugation can vary, depending on the tissue type being processed. In some embodiments, the cell suspension is centrifuged for a period of 3-30 minutes and at a speed of from 500 g-2,000 g. In some embodiments, the cell suspension is centrifuged for 10-25 minutes at a speed of 1,000 g-1,800 g. In some embodiments, the cell suspension is centrifuged for 10 minutes at 1,200 g. In some embodiments, the cell suspension is centrifuged for 7 minutes at 1,200 g. In some embodiments, the cell suspension is centrifuged for 5 minutes at 1,200 g. In some embodiments, the cell suspension is centrifuged for 3 minutes at 1,200 g. In some embodiments, the cell suspension is centrifuged for 10 minutes at 900 g. In some embodiments, the cell suspension is centrifuged for 7 minutes at 900 g. In some embodiments, the cell suspension is centrifuged for 5 minutes at 900 g. In some embodiments, the cell suspension is centrifuged for 3 minutes at 900 g. In some embodiments, the cell suspension is centrifuged for 10 minutes at 600 g. In some embodiments, the cell suspension is centrifuged for 7 minutes at 600 g. In some embodiments, the cell suspension is centrifuged for 5 minutes at 600 g. In some embodiments, the cell suspension is centrifuged for 3 minutes at 600 g.

There are numerous means by which multiple cell types present in the cell suspension can be separated from each other via centrifugation. For example, a density gradient may be utilized such that, during centrifugation, cells will separate into bands according to their specific densities. Additionally, size exclusion protocols can be used to separate cells via size. Additionally, separation can begin prior to centrifugation, for example by allowing the processed tissue sample to settle and separating undesired cellular debris from the desired cellular fraction prior to centrifugation. The type of separation technique used can vary based on the desired cellular fraction to be isolated.

Once the desired cell fraction is isolated, it may be resuspended for administration to the subject from which it was derived 125. In some embodiments, the desired cellular fraction is resuspended in a small volume of fluid obtained from the centrifuge tube. In some embodiments the desired cellular fraction is resuspended in sterile saline.

In one aspect, the desired cellular fraction is stem cells and the tissue from which the stem cells are derived is fat.

A first embodiment of a method of processing stem cells from fat follows:

Fat is obtained from a patient via liposuction. The liposuction can be performed via a syringe, where the fat is removed from the patient directly via a needle, or via a liposuction machine. The amount of fat removed during the liposuction can vary, depending on the number of stem cells desired. In some embodiments, the liposuction is a mini-liposuction, in which about 30 cc to about 50 cc of fat is removed from the patient. In some embodiments, the liposuction is a micro-liposuction, in which about 5 cc to about 29 cc of fat is removed from the patient. In some embodiments, the liposuction is a typical clinical liposuction, in which case 300 cc of fat or more is removed from the patient.

Once the fat is removed from the patient, it is transferred into a sterile processing container or cartridge. The transfer occurs via sterile means, as described herein. In some embodiments, the fat is removed from the patient via a syringe and is transferred from the syringe to the processing container or cartridge by attaching male and female luer lock connectors to each other between the syringe and the processing container or cartridge. In some embodiments, the fat is removed from the patient via a syringe and the syringe is sterile-docked within the processing container or cartridge by attaching male and female luer lock connectors to each other between the syringe and the container or cartridge. In some embodiments, the fat is removed from the patient via a syringe and is transferred from the syringe to the processing container or cartridge by attaching male and female luer lock connectors to each other between the syringe and the processing container or cartridge within the cartridge. In some embodiments, the fat is removed from the patient via a liposuction device and is transferred from the liposuction device to the processing container or cartridge by sterile-docking the liposuction device and the processing container or cartridge using a sterile connection device.

In some embodiments, the transfer can occur via gravity flow. In some embodiments, the transfer can occur mechanically, for example by physically depressing the plunger of a syringe and forcing the fat from the interior of the syringe into the interior of the processing container or cartridge. In some embodiments, the transfer can occur via a device, such as a pump.

The volume of the container or cartridge used to receive the fat can vary with the amount of fat obtained from the patient. In some embodiments, 30 cc to 50 cc of fat, removed via a mini-liposuction, is transferred to a container or cartridge having a volume of 9 fluid ounces to 19 fluid ounces.

A volume of sterile saline equal to the amount of fat removed from the patient is then transferred to the container or cartridge in order to wash the fat. By way of example, if 30 cc of fat were removed from the patient, then 30 mL of sterile saline are used to wash the sample. In some embodiments, a volume of sterile saline greater than the amount of fat removed from the patient is then transferred to the container or cartridge in order to wash the fat. By way of example, if 30 cc of fat were removed from the patient, then 35 mL of sterile saline are used to wash the sample. In some embodiments, a volume of sterile saline less than the amount of fat removed from the patient is then transferred to the container or cartridge in order to wash the fat. By way of example, if 30 cc of fat were removed from the patient, then 25 mL of sterile saline are used to wash the sample. In some embodiments, a combination of sterile saline volumes is added to the amount of fat in order to wash the fat. The transfer of the saline to the container or cartridge is performed so as to maintain the sterility of the system, as described herein. In some embodiments, the sterile saline is transferred to the container or cartridge by attaching male and female luer lock connectors to each other between the container holding the sterile saline and the processing container or cartridge. In some embodiments, the sterile saline is transferred to the container or cartridge by sterile-docking the sterile saline container and the processing container or cartridge using a sterile connection device.

Washing is performed by gently shaking or swirling the container or cartridge containing the fat and sterile saline.

The container or cartridge is then positioned in such a way so as to allow the (now washed) fat to separate from the sterile saline. Because the fat is less dense than the saline, it will rise and float on top of the saline. The amount of time required for separation to occur will vary depending on the individual make-up of the fat sample. In some embodiments, separation can occur from 1 to 30 minutes. In some embodiments, separation can occur from 1 to 15 minutes. In some embodiments, separation can occur from 1 to 10 minutes. In some embodiments, separation can occur from 1 to 5 minutes. In some embodiments, separation can occur from 10 seconds to 1 minute.

The saline is then drained from the container or cartridge as completely as possible, so only the fat remains. Drainage can occur via various means, depending on the type of container or cartridge utilized in the method. In some embodiments, the saline is drained out of the container or cartridge via a tube located at the bottom of the container or cartridge. Draining can proceed actively, using either a syringe or a pump, or passively via gravity flow. In some embodiments, the draining occurs so as to maintain the integrity of the sterile system, as described herein.

Washing is repeated until the fat is a golden color and the saline is only slightly cloudy after completion of a wash. In some embodiments, washing occurs 1-5 times, in some embodiments 1~4 times, in some embodiments 1-3 times, in some embodiments 1-2 times, and in some embodiments 1 time.

Once washing is complete, the fat is ready for processing.

Optionally, sterile saline is added to the bag for processing, though this is not required. The addition of saline will provide room for cells and/or small clusters of cells to freely move away from each other during processing, thereby helping to break the fat down into individual cells. If saline is added, it is added in a manner that will maintain the integrity of the sterile system, as described herein.

The volume of saline optionally added can vary. In some embodiments, the volume of saline added ranges from none to 2 times the volume of fat removed from the patient. In some embodiments, an equal amount of saline is used (e.g., 30 mL of saline for 30 cc of fat).

Excess air is removed from the container or cartridge using a pump or syringe. In some embodiments, the excess air is removed from the same tube located at the bottom of the container or cartridge from which the sterile saline wash is drained. In some embodiments, the air is drained in a manner that maintains the integrity of the sterile, closed system, as described herein.

Figure 2:
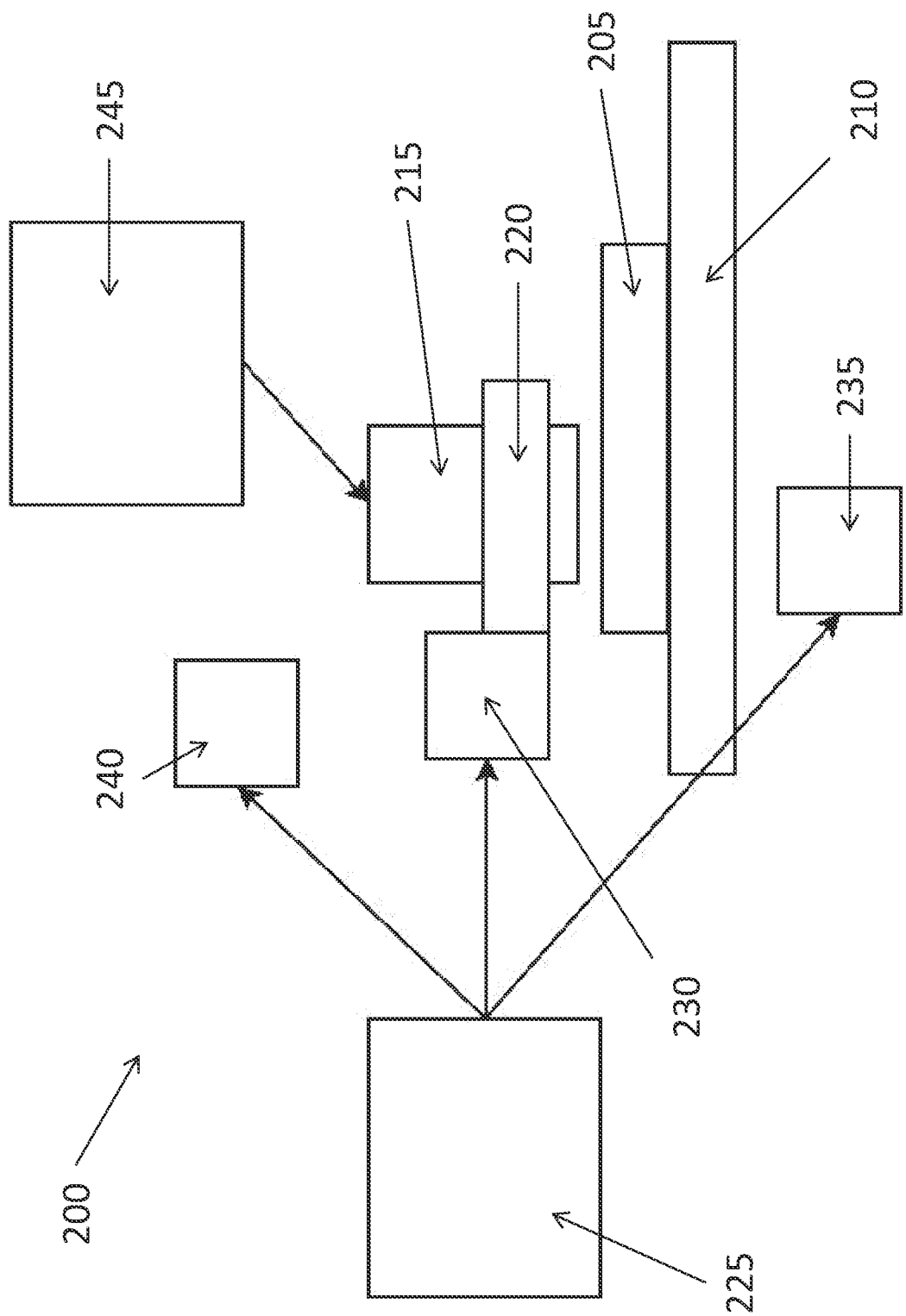
FIG. 2 depicts a representative example of an extracorporeal shockwave device suitable for use in the systems and methods provided by the present disclosure.

The processing container or cartridge is then moved to a processing apparatus. An example of a suitable processing apparatus 200 is shown in FIG. 2. In the depicted embodiment, the processing container or cartridge 205 is secured onto a rigid platform 210 for processing. The platform 210 controls the movement of the container or cartridge 205 during ESW processing.

The platform 210 can be made of any suitable, rigid material including wood, metal, plastic, acrylic and the like. In some embodiments, the platform 210 is made of wood.

The processing apparatus 200 houses a shockwave applicator 215 capable of delivering shockwaves to the interior of the container or cartridge 205. The shockwave applicator 215 is housed on the processing apparatus 200 via an applicator platform 220. The applicator platform 220 and the shockwave applicator 215 are maintained a distance away from the fat contained within the container or cartridge 205 such that the shockwave applicator 215 is never placed in direct contact with the fat. This ensures that the shockwaves delivered to the fat are extracorporeal, or ESW. In some embodiments, the shockwave applicator 215 may be placed in direct contact with the processing container or cartridge

205. In such embodiments, the walls of the container or cartridge 205 ensure that the shockwave applicator 215 never makes direct contact with the fat.

Movement of the applicator platform 220, and this the shockwave applicator 215, can occur in three directional planes, X, Y and Z, each of which is controlled by its own motor: an X plane motor 230, a Y plane motor 235 and a Z plane motor 240. In some embodiments, these motors are NEMA 17 stepper motors. Each of motors 230, 235 and 240 is controlled by a motor controller 225, which enables movement of the applicator platform 220 and shockwave applicator 215 in three dimensions over and around the container or cartridge 205. In some embodiments, the motors are controlled by an Arduino microprocessor v6 board programmed with Marlin firmware. In some embodiments, the motors are controlled by an Arduino v6 board with Marlin firmware. In some embodiments, only the X plane motor 230 is used. In some embodiments, only the Y plane motor 235 is used. In some embodiments, only the Z plane motor 240 is used. In some embodiments, only the X plane motor 230 is used. In some embodiments, only the X plane motor 230 and the Y plane motor 235 are used. In some embodiments, only the X plane motor 230 and the Z plane motor 240 are used. In some embodiments, only the Y plane motor 235 and the Z plane motor 240 are used. In some embodiments, the X plane motor 230, the Y plane motor 235 and the Z plane motor 240 are used.

This three dimensional movement of the applicator platform 220 and shockwave applicator 215 allows all of the fat in the extracted sample to be exposed to the extracorporeal shockwaves during processing.

Shockwaves are then delivered from the shockwave applicator 215, through a transmission gel or membrane containing a transmission gel, through the walls of the container or cartridge 205, and to the fat sample in order to break apart the fat, freeing small clusters of cells and individual cells from the fat. In some embodiments, the transmission gel is REF 4248 Conductor Transmission Gel manufactured for Chattanooga by DJO, LLC, 1430 Decision Street, Vista, CA 92081, USA. In those embodiments in which sterile saline is added to the fat prior to processing, the small clusters of cells and/or individual cells freed from the fat will move into the saline.

The shockwave applicator 215 is powered by a shockwave generator 245, which produces the ESW that are transmitted to the fat via the shockwave applicator 215. In some embodiments, the shockwave generator is a MasterPuls MP100 made by Storz Medical AG, 8274 Tagerwilen, Switzerland. In some embodiments, the shockwave generator is the BS-SWT2X made by Lumsail Industrial Inc., 4/F, No. 9Yi, Lane 2, Suide Road, Shanghai, 200331, China.

The power of the ESW delivered to the fat can vary. For instance, it may be necessary to increase the power of the ESW in order to penetrate the walls of a thick walled container or cartridge 205. Generally, the power of the ESW delivered to the fat can vary depending upon the thickness of the walls of the container or cartridge 205 and/or the material the container or cartridge 205 are made of. In some embodiments, the power of the ESW delivered to the fat ranges from 0.5 to 5.0 bars. In some embodiments, the power of the ESW delivered to the fat ranges from 1.0 to 4.5 bars. In some embodiments, the power of the ESW delivered to the fat ranges from 1.5 to 4.0 bars. In some embodiments, the power of the ESW delivered to the fat ranges from 2.0 to 3.5 bars. In some embodiments, the container 205 is a vinyl bag having walls that are 0.25 mm thick and the power level of the ESW ranges from 2.0 to 2.5 bars.

The area covered by the ESW delivered by the shockwave applicator 215 can vary. The greater the area covered by the shockwave applicator 215, the greater the surface area of the fat that is exposed to ESW. In some embodiments, the total area covered by the shockwave applicator 215 ranges from 1 $cm^2$ to 100 $cm^2$, in some embodiments from 1 $cm^2$ to 90 $cm^2$, in some embodiments from 1 $cm^2$ to 80 $cm^2$, in some embodiments from 1 $cm^2$ to 70 $cm^2$, in some embodiments from 1 $cm^2$ to 60 $cm^2$, in some embodiments from 1 $cm^2$ to 50 $cm^2$, in some embodiments from 1 $cm^2$ to 40 $cm^2$, in some embodiments from 1 $cm^2$ to 30 $cm^2$, in some embodiments from 1 $cm^2$ to 20 $cm^2$, in some embodiments from 1 $cm^2$ to 10 $cm^2$, and in some embodiments from 1 $cm^2$ to 5 $cm^2$. In some embodiments, the total area covered by the shockwave applicator 215 is 5 $cm^2$.

In one embodiment, the container 205 is a 19 oz vinyl bag having walls 0.25 mm thick, the total amount of fat obtained from the patient is 30 cc, and an optional addition of 30 mL of saline (an equal volume of the fat sample) is added to the vinyl bag prior to processing. In this embodiment, the total area of the bag, and thus the total amount of the fat sample, exposed to the ESW is approximately 5 $cm^2$.

The number of shockwaves delivered to the fat sample can vary. In some embodiments, the total number of shockwaves ranges from 5,000 to 100,000, in some embodiments from 10,000 to 50,000, in some embodiments from 10,000 to 25,000, and in some embodiments from 10,000 to 20,000. In some embodiments, the total number of shockwaves is 25,000.

In this embodiment, stem cells are separated from the fat sample obtained from the patient. Using an applicator tip of 5 $cm^2$ on the shockwave applicator 215, a shockwave number range of from 10,000 to 50,000 at a bar range of 2.0 to 2.5 is sufficient to separate both stem cells and a stromal vascular fraction from fat. As used herein, "stromal vascular fraction" means a cellular fraction obtained from processes tissue samples that comprises the cells obtained from separating and dissociating the cellular fraction, which in some embodiments is fat. The stromal vascular fraction comprises, without limitation, stem cells, growth factors and progenitor cells, among other things.

After the ESW are applied to the fat sample, the container or cartridge is subjected to mechanical agitation for a brief period of time. In some embodiments, the mechanical agitation is shaking. In some embodiments, the mechanical agitation is inverting the container or cartridge 205 one or more times. In some embodiments the short period of time ranges from 1 to 30 seconds, in some embodiments from 1 to 15 seconds, and in some embodiments from 1 to 10 seconds. In some embodiments, the short period of time is approximately 10 seconds. Agitation allows the stem cells and stromal vascular fraction that have been liberated from the fat to separate from the fatty cellular debris and any lingering fat tissue that may still be present in the container or cartridge 205.

The container or cartridge 205 is then positioned in such a way so as to allow the (now processed) fat to separate from the sterile saline that now contains stem cells and stromal vascular fraction that have been separated from the fat by the ESW. Because the fat is less dense than the stem cell-containing saline, it will rise and float on top of the saline. The amount of time required for separation to occur will vary depending on the individual make-up of the fat sample. In some embodiments, separation can occur from 1 to 30 minutes. In some embodiments, separation can occur from 1 to 15 minutes. In some embodiments, separation can occur from 1 to 10 minutes. In some embodiments, separation can occur from 1 to 5 minutes. In some embodiments, separation can occur from 10 seconds to 1 minute. In some embodiments, separation can occur in less than 1 minute.

The stem cells have now been separated from the fat sample and are now suspended in the sterile saline layer.

The stem cell-containing saline layer is then removed from the container or cartridge 205 as completely as possible, so only the fat remains. Removal can occur via various means, depending on the type of container or cartridge 205 utilized in the method. In some embodiments, the saline is drained out of the container or cartridge 205 via a tube located at the bottom of the container or cartridge 205. Draining can proceed actively, using either a syringe or a pump, or passively via gravity flow. In some embodiments, the stem-cell containing layer is removed in a manner that will maintain the integrity of the closed, sterile environment, as described herein.

In some embodiments, the stem cell-containing saline layer is passed through a filter during removal from the container or cartridge 205. The size of the filter can vary. In some embodiments, the filter size ranges from 40 μm to 100 μm. In some embodiments, the filter size is 70 μm. In various embodiments, the filter is nylon.

Either after or during removal from the container or cartridge 205, the stem cell-containing saline is moved into one or more centrifuge tubes. In some embodiments, movement occurs in a manner that maintains the integrity of the closed, sterile environment, as described herein. Centrifugation follows, in order to concentrate the stem cells into a pellet at the bottom of the centrifuge tube.

The stem cells are concentrated by centrifugation at 500 g to 1,600 g for 3 to 10 minutes. In some embodiments, the stem cells are concentrated by centrifugation for 10 minutes at 1,200 g.

The fluid is removed from the tube, leaving only the stem cells at the bottom. The fluid may be removed by decanting, aspiration or similar means.

A small amount of fluid is put into the centrifuge tube(s) in order to resuspend the stem cells. In some embodiments, the amount of fluid added to the centrifuge tubes ranges from 1 mL to 5 mL. In some embodiments, the fluid is saline, platelet-rich-plasma, hyaluronan, a fixing gel, hydrogel, scaffold, fibrin, glue, or combinations of any of the foregoing. In some embodiments, the cells are resuspended in the centrifugation aspirate.

With the stem cells floating in suspension, they are ready for use. Such use can include, without limitation, reintroduction into the patient from which they were derived, cryopreservation, expansion, and the like. In some embodiments, the concentrated, resuspended stem cells are moved into a syringe, via a hypodermic needle, for patient use. In some embodiments the concentrated, resuspended stem cells are seeded into a tissue-scaffold for growing into, cardiac, muscle, bone, cartilage, liver, kidney, or other tissue and organ structures. In some embodiments the concentrated, resuspended stem cells are transformed into induced-pluripotent stem cells by causing them to express pluripotency transcription factors.

A second embodiment of a method of processing stem cells from fat follows:

Fat is obtained from a patient via liposuction. The liposuction can be performed via a syringe, where the fat is removed from the patient directly via a needle, or via a liposuction machine. The amount of fat removed during the liposuction can vary, depending on the number of stem cells desired. In some embodiments, the fat is removed from the patient via a syringe and the syringe is sterile-docked within the cartridge by attaching male and female luer lock connectors to each other between the syringe and the cartridge. In some embodiments, the fat is removed from the patient via a syringe and is transferred from the syringe to the processing container or cartridge by attaching male and female luer lock connectors to each other between the syringe and the processing container or cartridge within the cartridge. In some embodiments, the liposuction is a mini-liposuction, in which about 30 cc to about 50 cc of fat is removed from the patient. In some embodiments, the liposuction is a micro-liposuction, in which about 5 cc to about 29 cc of fat is removed from the patient. In some embodiments, the liposuction is a typical clinical liposuction, in which case 300 cc of fat or more is removed from the patient.

Once the fat is removed from the patient, it is transferred into a sterile processing container or cartridge. The transfer occurs via sterile means, as described herein. In some embodiments, the fat is removed from the patient via a syringe and is transferred from the syringe to the processing container or cartridge by attaching male and female luer lock connectors to each other between the syringe and the processing container or cartridge. In some embodiments, the fat is removed from the patient via a liposuction device and is transferred from the liposuction device to the processing container or cartridge by sterile-docking the liposuction device and the processing container or cartridge using a sterile connection device.

In some embodiments, the transfer can occur via gravity flow. In some embodiments, the transfer can occur mechanically, for example by physically depressing the plunger of a syringe and forcing the fat from the interior of the syringe into the interior of the processing container or cartridge. In some embodiments, the transfer can occur via a device, such as a pump.

The volume of the container or cartridge used to receive the fat can vary with the amount of fat obtained from the patient. In some embodiments, 30 cc to 50 cc of fat, removed via a mini-liposuction, is transferred to a container or cartridge having a volume of 9 fluid ounces to 19 fluid ounces.

A volume of sterile saline equal to the amount of fat removed from the patient is then transferred to the container or cartridge in order to wash the fat. By way of example, if 30 cc of fat were removed from the patient, then 30 mL of sterile saline are used to wash the sample. In some embodiments, the fat is removed from the patient via a syringe and the syringe is sterile-docked within the cartridge by attaching male and female luer lock connectors to each other between the syringe and the cartridge. In some embodiments, the fat is removed from the patient via a syringe and is transferred from the syringe to the processing container or cartridge by attaching male and female luer lock connectors to each other between the syringe and the processing container or cartridge within the cartridge. The transfer of the saline to the container or cartridge is performed so as to maintain the sterility of the system, as described herein. In some embodiments, the sterile saline is transferred to the container or cartridge by attaching male and female luer lock connectors to each other between the container holding the sterile saline and the processing container or cartridge. In some embodiments, the sterile saline is transferred to the container or cartridge by sterile-docking the sterile saline container and the processing container or cartridge using a sterile connection device.

Washing is performed by gently shaking or swirling the container or cartridge containing the fat and sterile saline.

The container or cartridge is then positioned in such a way so as to allow the (now washed) fat to separate from the sterile saline. Because the fat is less dense than the saline, it will rise and float on top of the saline. The amount of time required for separation to occur will vary depending on the individual make-up of the fat sample. In some embodiments, separation can occur from 1 to 30 minutes. In some embodiments, separation can occur from 1 to 15 minutes. In some embodiments, separation can occur from 1 to 10 minutes. In some embodiments, separation can occur 1 to 5 minutes.

The saline is then drained from the container or cartridge as completely as possible, so only the fat remains. Drainage can occur via various means, depending on the type of container or cartridge utilized in the method. In some embodiments, the saline is drained out of the container or cartridge via a tube located at the bottom of the container or cartridge. Draining can proceed actively, using either a syringe or a pump, or passively via gravity flow. In some embodiments, the draining occurs so as to maintain the integrity of the sterile system, as described herein.

Washing is repeated until the fat is a golden color and the saline is only slightly cloudy after completion of a wash. In some embodiments, washing occurs 1-5 times, in some embodiments 1-4 times, in some embodiments 1-3 times, in some embodiments 1-2 times, and in some embodiments 1 time.

Once washing is complete, the fat is ready for processing.

Optionally, sterile saline is added to the bag for processing, though this is not required. The addition of saline will provide room for cells and/or small clusters of cells to freely move away from each other during processing, thereby helping to break the fat down into individual cells. If saline is added, it is added in a manner that will maintain the integrity of the sterile system, as described herein.

The volume of saline optionally added can vary. In some embodiments, the volume of saline added ranges from none to 2 times the volume of fat removed from the patient. In some embodiments, an equal amount of saline is used (e.g., 30 mL of saline for 30 cc of fat).

Excess air is removed from the container or cartridge using a pump or syringe. In some embodiments, the excess air is removed from the same tube located at the bottom of the container or cartridge from which the sterile saline wash is drained. In some embodiments, the air is drained in a manner that maintains the integrity of the sterile, closed system, as described herein.

Figure 3:
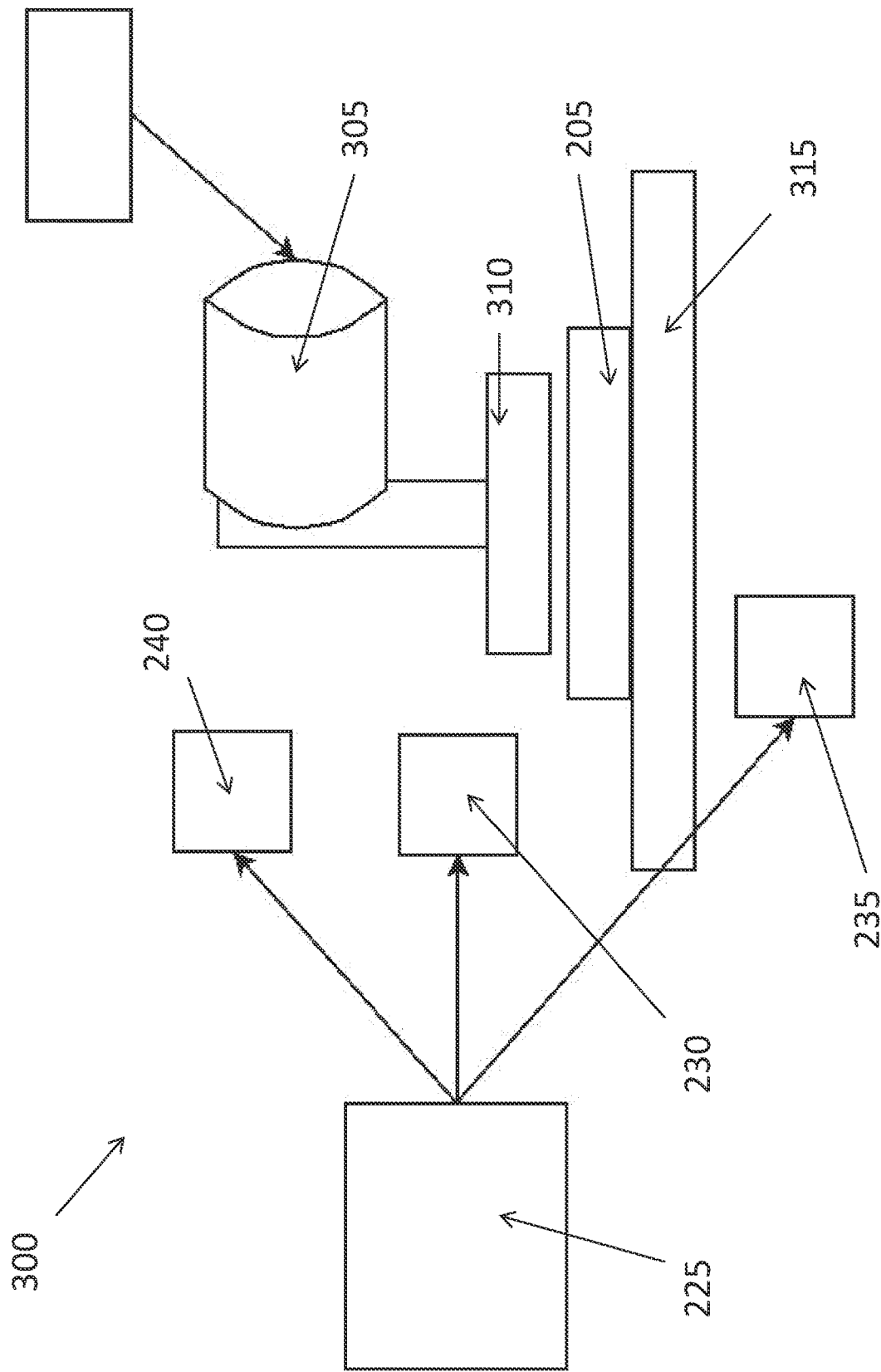
FIG. 3 depicts a representative example of a mechanical impact device suitable for use in the systems and methods provided by the present disclosure.

The processing container or cartridge is then moved to a processing apparatus. An example of a suitable processing apparatus 300 is shown in FIG. 3. In the depicted embodiment, the processing container or cartridge 205 is secured onto a rigid platform 315 for processing. The platform 315 controls the movement of the container or cartridge 205 during processing.

The platform 315 can be made of any suitable, rigid material including wood, plastic, and the like. In some embodiments, the platform 315 is made of wood.

In this embodiment, mechanical impacts are used to break up the fat tissue and release stem cells.

The mechanical impacts are generated by a motor 305 that drives an impact arm 310 that makes physical contact with the container or cartridge 205 containing the fat to be processed. In this embodiment, the motor 305 drives the impact arm 310 such that the impact arm 310 articulates up and down, making contact with the container or cartridge 205 at the bottom of its range of motion. In some embodiments, the motor is a 4.5 Amp motor from model BDEJS300C made by Black and Decker, 1000 Stanley Drive, New Britain, CT 06053, USA.

In some embodiments, the motor 305 is a variable speed motor that is adjustable to drive the impact arm at a rate ranging from 0 to 30,000 rpm, in some embodiments from 0 to 20,000 rpm, in some embodiments from 0 to 10,000 rpm, and in some embodiments from 0 to 5,000 rpm.

In some embodiments, the motor 305 comprises gearing capable of reducing the speed of the impact arm 310 when the motor 305 is operating at full speed (in some embodiments, 30,000 rpm) in order to generate more torque. When this is done, the momentum generated by the impact arm 310 is transferred to the tissue in the container or cartridge 205. This greatly increases the rate at which the fat tissue is broken down and stem cells are liberated from the fatty tissue.

In one embodiment, the motor 305 is geared to allow for a 10 to 1 reduction in speed from 30,000 rpm to 3,000 rpm. In this embodiment, the motor 305 comprises a gear diameter of 0.75 inches, which allows for this 10 to 1 reduction. At 3,000 rpm, and a gear diameter of 0.75 inches, the impact arm 310 reaches a speed of 117.8 inches per second—the speed at which the impact arm 310 articulates back and forth and, thus, makes contact with the container or cartridge 205. The speed at which the impact arm 310 is capable of making contact with the container or cartridge 205 allows for greatly reduced processing times. This confers a significant advantage over known or existing tissue processing techniques, which require very lengthy processing times.

The tissue is exposed to the mechanical impacts until the fat is broken down to a desired level, or until the desired amount of stem cells has been liberated from the fat. In some embodiments, the fat sample is processed in 30 minutes or less. In some embodiments, the fat sample is processed between 30 seconds and 30 minutes, in some embodiments between 30 second and 20 minutes, in some embodiments between 30 seconds and 10 minutes and in some embodiments between 30 seconds and 5 minutes.

Movement of the platform 315 occurs in three directional planes, X, Y and Z, each of which is controlled by its own motor: an X plane motor 230, a Y plane motor 235 and a Z plane motor 240. In some embodiments, only the X plane motor 230 is used. In some embodiments, only the Y plane motor 235 is used. In some embodiments, only the Z plane motor 240 is used. In some embodiments, only the X plane motor 230 is used. In some embodiments, only the X plane motor 230 and the Y plane motor 235 are used. In some embodiments, only the X plane motor 230 and the Z plane motor 240 are used. In some embodiments, only the Y plane motor 235 and the Z plane motor 240 are used. In some embodiments, the X plane motor 230, the Y plane motor 235 and the Z plane motor 240 are used. Each of motors 230, 235 and 240 is controlled by a motor controller 225, which enables movement of the platform 315 in three dimensions.

This up-to three dimensional movement of the platform 315 allows all of the fat in the extracted sample to be exposed to the mechanical impacts during processing, and for optimal positioning of the sample and processing apparatus.

The length, area of impact surface, number of impact surfaces, and shape of the impact arm 310 can vary. In some embodiments, increasing the total area of the impact surface and/or the total number of impact surfaces reduces the amount of time required to process a fat sample.

The container or cartridge 205 is then positioned in such a way so as to allow the (now processed) fat to separate from the sterile saline that now contains stem cells that have been separated from the fat by the mechanical impacts. Because the fat is less dense than the saline, it will rise and float on top of the saline. The amount of time required for separation to occur will vary depending on the individual make-up of the fat sample. In some embodiments, separation can occur from 1 to 30 minutes. In some embodiments, separation can occur from 1 to 15 minutes. In some embodiments, separation can occur from 1 to 10 minutes. In some embodiments, separation can occur 1 to 5 minutes. In some embodiments, separation can occur in less than 1 minute. In some embodiments, separation can occur from 10 seconds to 1 minute. In some embodiments, separation can occur in less than 1 minute.

The stem cells and stromal vascular fraction have now been separated from the fat sample and are now suspended in the saline.

The stem cell-containing saline layer is then removed from the container or cartridge 205 as completely as possible, so only the fat remains. Removal can occur via various means, depending on the type of container or cartridge 205 utilized in the method. In some embodiments, the saline is drained out of the container or cartridge 205 via a tube located at the bottom of the container or cartridge 205. Draining can proceed actively, using either a syringe or a pump, or passively via gravity flow. In some embodiments, the stem-cell containing layer is removed in a manner that will maintain the integrity of the closed, sterile environment, as described herein.

In some embodiments, the stem cell-containing saline is passed through a filter during removal from the container or cartridge 205. The size of the filter can vary. In some embodiments, the filter size ranges from 40 μm to 100 μm. In some embodiments, the filter size is 70 μm. In various embodiments, the filter is nylon.

Either after or during removal from the container or cartridge 205, the stem cell-containing saline is moved into one or more centrifuge tubes. In some embodiments, movement occurs in a manner that maintains the integrity of the closed, sterile environment, as described herein. Centrifugation follows, in order to concentrate the stem cells into a pellet at the bottom of the centrifuge tube.

The stem cells are concentrated by centrifugation at 500 g to 1,600 g for 3 to 10 minutes. In some embodiments, the stem cells are concentrated by centrifugation for 10 minutes at 1,200 g.

The fluid is removed from the tube, leaving only the stem cells at the bottom. The fluid may be removed by decanting, aspiration or similar means.

A small amount of fluid is put into the centrifuge tube(s) in order to resuspend the stem cells. In some embodiments, the amount of fluid added to the centrifuge tubes ranges from 1 mL to 5 mL. In some embodiments, the fluid is saline, platelet-rich-plasma, hyaluronan, a fixing gel, hydrogel, scaffold, fibrin glue, glue, or combinations of any of the foregoing. In some embodiments, the cells are resuspended in the centrifugation aspirate.

With the stem cells in suspension, they are ready for use. Such use can include, without limitation, reintroduction into the patient from which they were derived, cryopreservation, expansion, and the like. In some embodiments, the concentrated, resuspended stem cells are moved into a syringe, via a hypodermic needle, for patient use. In some embodiments the concentrated, resuspended stem cells are seeded into a tissue-scaffold for growing into, cardiac, muscle, bone, cartilage, liver, kidney, or other tissue and organ structures. In some embodiments the concentrated, resuspended stem cells are transformed into induced-pluripotent stem cells by causing them to express pluripotency transcription factors.

In the first and second methods described above, the container or cartridge and mechanical energy sources are movable. In some embodiments, the fat is pumped through a chamber that is placed under the ESW or impact surface. In these embodiments, both the bag and the mechanical energy sources are fixed in place and the tissue is passed through the chamber to be exposed to the ESW and/or mechanical energy source.

A third embodiment of a method of processing stem cells from fat follows:

Fat is obtained from a patient via liposuction. The liposuction can be performed via a syringe, where the fat is removed from the patient directly via a needle, or via a liposuction machine. The amount of fat removed during the liposuction can vary, depending on the number of stem cells desired. In some embodiments, the liposuction is a mini-liposuction, in which about 30 cc to about 50 cc of fat is removed from the patient. In some embodiments, the liposuction is a micro-liposuction, in which about 5 cc to about 29 cc of fat is removed from the patient. In some embodiments, the liposuction is a typical clinical liposuction, in which case 300 cc of fat or more is removed from the patient.

Once the fat is removed from the patient, it is transferred into a sterile processing cartridge. The transfer occurs via sterile means, as described herein. In some embodiments, the fat is removed from the patient via a syringe and is transferred from the syringe to the processing cartridge by attaching male and female luer lock connectors to each other between the syringe and the processing cartridge. In some embodiments, the fat is removed from the patient via a syringe and the syringe is sterile-docked within the cartridge by attaching male and female luer lock connectors to each other between the syringe and the cartridge. In some embodiments, the fat is removed from the patient via a syringe and is transferred from the syringe to the processing container or cartridge by attaching male and female luer lock connectors to each other between the syringe and the processing container or cartridge within the cartridge. In some embodiments, the fat is removed from the patient via a liposuction device and is transferred from the liposuction device to the processing cartridge by sterile-docking the liposuction device and the processing cartridge using a sterile connection device.

In some embodiments, the transfer can occur via gravity flow. In some embodiments, the transfer can occur mechanically, for example by physically depressing the plunger of a syringe and forcing the fat from the interior of the syringe into an interior chamber of the processing cartridge. In some embodiments, the transfer can occur via a device, such as a pump.

The volume of the interior chamber of the cartridge 400, 500 that receives the fat (see, for example, the cartridge embodiments provided in FIGS. 4 and 5) can vary with the amount of fat obtained from the patient. In some embodiments, 30 cc to 50 cc of fat, removed via a mini-liposuction, is transferred to an adipose chamber 405, 505 of a cartridge 400, 500.

In this embodiment, the fat is injected into a specific component 405, 505 of a self-contained cartridge 400, 500, the cartridge 400, 500 designed to accommodate processing of the fat sample entirely within the cartridge 400, 500, without exposing the sample to the outside environment. In some embodiments, the adipose chamber 405, 505 located within the cartridge 400, 500 that receives the fat is a flexible bag having a volume of 9 fluid ounces to 19 fluid ounces.

In various aspects, the cartridge 400, 500 is designed for use with any of the ESW or mechanical impact devices and methods disclosed herein. In some embodiments, the processing is performed by a machine that runs several of the processing steps described below automatically. In some embodiments, the processing is performed by a user, who manually performs the steps described below. In both embodiments, the processing is controlled externally, such that the internal processing of the cartridge 400, 500 is performed in a sterile manner, without the sample ever being exposed to the outside environment.

In the depicted embodiments, the fat sample is introduced into the adipose chamber 405, 505 by passing it through a first one-way valve 410, 510. The direction of the first one-way flow valve 410, 510 is as depicted—into the interior of the adipose chamber 405, 505. In some embodiments, the fat is introduced into the interior chamber of the adipose chamber 405, 505 by attaching male and female luer lock connectors to each other between the container holding the fat after extrication from the patient and the first one-way valve 410, 510 of the processing cartridge 400, 500. In some embodiments, the fat is removed from the patient via a liposuction device and is transferred from the liposuction device to the processing cartridge by sterile-docking the liposuction device and the processing cartridge using a sterile connection device.

Once inside the adipose chamber 405, 505, the fat is washed prior to processing. The cartridge 400, 500 contains a fluid reservoir 415, 515 filled with sterile saline, in some embodiments sterile 1× phosphate buffered saline, that is used to wash the tissue. To introduce the sterile saline into the interior of the adipose chamber 405, 505, the saline is passed through a second one-way valve 420, 520 into the interior of the adipose chamber 405, 505. The direction of the flow is as indicated. The saline is moved into the interior of the adipose chamber 405, 505 via use of an external actuator 425, 525 that moves a first plunger 430, 530 in order to force the saline through the first one-way valve 420, 520. In some embodiments, the external actuator 425, 525 is operated manually by a user, who depresses the actuator 425, 525 until a desired amount of saline is passed through the second one-way valve 420, 520 into the interior of the adipose chamber 405, 505. In some embodiments, movement of the external actuator 425, 525 is automated and an external machine causes the external actuator 425, 525 to move in the direction shown, thereby metering a desired amount of saline through the second one-way valve 420, 520 into the interior of the adipose chamber 405, 505.

Washing is performed by gently shaking or swirling the cartridge 400, 500 containing the fat and sterile saline.

The cartridge 400, 500 is then positioned in such a way so as to allow the (now washed) fat to separate from the sterile saline. In this embodiment, the cartridge 400, 500 has two variations. In some embodiments, the cartridge 400, 500 has a fixed vertical orientation such that the fat and saline wash contained in the adipose chamber 405, 505 will always naturally separate from each other via gravity, with the fat floating to the top of the adipose chamber 405, 505. In some embodiments, the cartridge 400, 500 has a horizontal orientation and is rotated vertically to allow the fat to float and separate from the saline wash. Because the fat is less dense than the saline, it will rise and float on top of the saline. The amount of time required for separation to occur will vary depending on the individual make-up of the fat sample. In some embodiments, separation can occur from 1 to 30 minutes. In some embodiments, separation can occur from 1 to 15 minutes. In some embodiments, separation can occur from 1 to 10 minutes. In some embodiments, separation can occur from 1 to 5 minutes. In some embodiments, separation can occur from 10 seconds to 1 minute. In some embodiments, separation can occur in less than 1 minute.

The saline is then drained from the adipose chamber 405, 505 as completely as possible, so only the fat remains. Drainage can occur via various means, depending on the type of cartridge 400, 500 utilized in the method. In some embodiments, the saline is drained out of the adipose chamber 405, 505 and away from the cartridge 400, 500 via a tube located at the bottom of the adipose chamber 405, 505 that leads outside of the cartridge 400, 500. Draining can proceed actively, using either a syringe or a pump, or passively via gravity flow. In some embodiments, the draining occurs so as to maintain the integrity of the sterile system, as described herein.

Washing is repeated until the fat is a golden color and the saline is only slightly cloudy after completion of a wash. In some embodiments, washing occurs 1-5 times, in some embodiments 1–4 times, in some embodiments 1-3 times, in some embodiments 1-2 times, and in some embodiments 1 time.

In some embodiments, washing is repeated until the sterile saline is depleted from the fluid reservoir 415, 515. In some embodiments, washing is repeated until the saline wash in the adipose chamber 405, 505 is clear enough, after washing, for 50% to 100% of light to pass through the saline, indicating a high degree of clarity. In some embodiments, washing is repeated until a set number of wash cycles has been completed which, in some embodiments, is 1 to 5, in some embodiments 1 to 4, in some embodiments 1 to 3, in some embodiments 1 to 2, in some embodiments 1, in some embodiments 2, and in some embodiments 3 washes.

Once washing is complete, the fat is ready for processing.

The fat in the adipose chamber 405, 505 is processed according to one of the methods described above in methods 1 and 2, by subjecting the fat to ESW and/or mechanical impacts, in order to liberate stem cells from the fat. In some embodiments, the cartridge 400, 500 has an opening over the adipose chamber 405, 505 to allow for optimal process, so that the ESW and/or the force from the mechanical impacts is/are not passing through the rigid plastic exterior of the cartridge 400, 500. In such embodiments, the flexible adipose chamber 405, 505 wall is exposed for processing.

After tissue processing is complete, the fat is allowed to separate from the fluid and rise to the top. As noted above, in this embodiment the cartridge 400, 500 has two variations. In some embodiments, the cartridge 400, 500 has a fixed vertical orientation such that the processed fat and saline contained in the adipose chamber 405, 505 will always naturally separate from each other via gravity, with the fat floating to the top of the adipose chamber 405, 505. In some embodiments, the cartridge 400, 500 has a horizontal orientation and is rotated vertically to allow the fat to float and separate from the saline. Because the fat is less dense than the saline, it will rise and float on top of the saline. The stem cells that have been liberated form the fat are now contained in the saline layer.

The stem-cell containing saline is then moved from the adipose chamber 405, 505 to a cell reservoir 435, 535 located within the cartridge 400, 500, away from the fat, through a third one-way valve 440, 540. The saline is moved into the interior of the cell reservoir 435, 535 via use of a second external actuator 445, 545 that moves a second plunger 450, 550 in order to force the saline through the third one-way valve 440, 540. In the cell reservoir 435, 535, the second plunger 450, 550 is oriented in a completely closed configuration, such that the cell reservoir 435, 535 is completely closed. In this way, moving the second actuator 445, 545 moves the second plunger 450, 550 away from the third one-way valve 440, 540, creating a mild vacuum inside of the cell reservoir 435, 535 that pulls the stem cell containing saline layer out of the adipose chamber 405, 505, through the third one-way valve 440, 540 and into the interior of the cell reservoir 435, 535. In some embodiments, the second external actuator 445, 545 is operated manually by a user, who pulls the second actuator 445, 545 until the entirety of the stem cell-containing saline is pulled through the third one-way valve 440, 540 into the interior of the cell reservoir 435, 535. In some embodiments, movement of the second external actuator 445, 545 is automated and an external machine pulls the second external actuator 445, 545 to move the stem cell containing saline into the cell reservoir 435, 535.

In some embodiments, the stem cell containing saline is drawn through a mesh in order to filter out unwanted cellular debris left over from the processed fatty tissue. In some embodiments, the mesh is located in the adipose chamber 405, 505 where it covers the opening of the third one-way valve 440, 540. In some embodiments, the mesh is located in the interior of the cell reservoir 435, 535 where it covers the exit of the third one-way valve 440, 540. In some embodiments, the mesh is located in the interior of the cell reservoir where it covers the opening of a fourth one-way valve 455, 555. In some embodiments, the pores in the mesh range in size from 40 μm to 100 μm and in some embodiments the pores are 70 μm in size. In some embodiments, the mesh is nylon.

Figure 4:
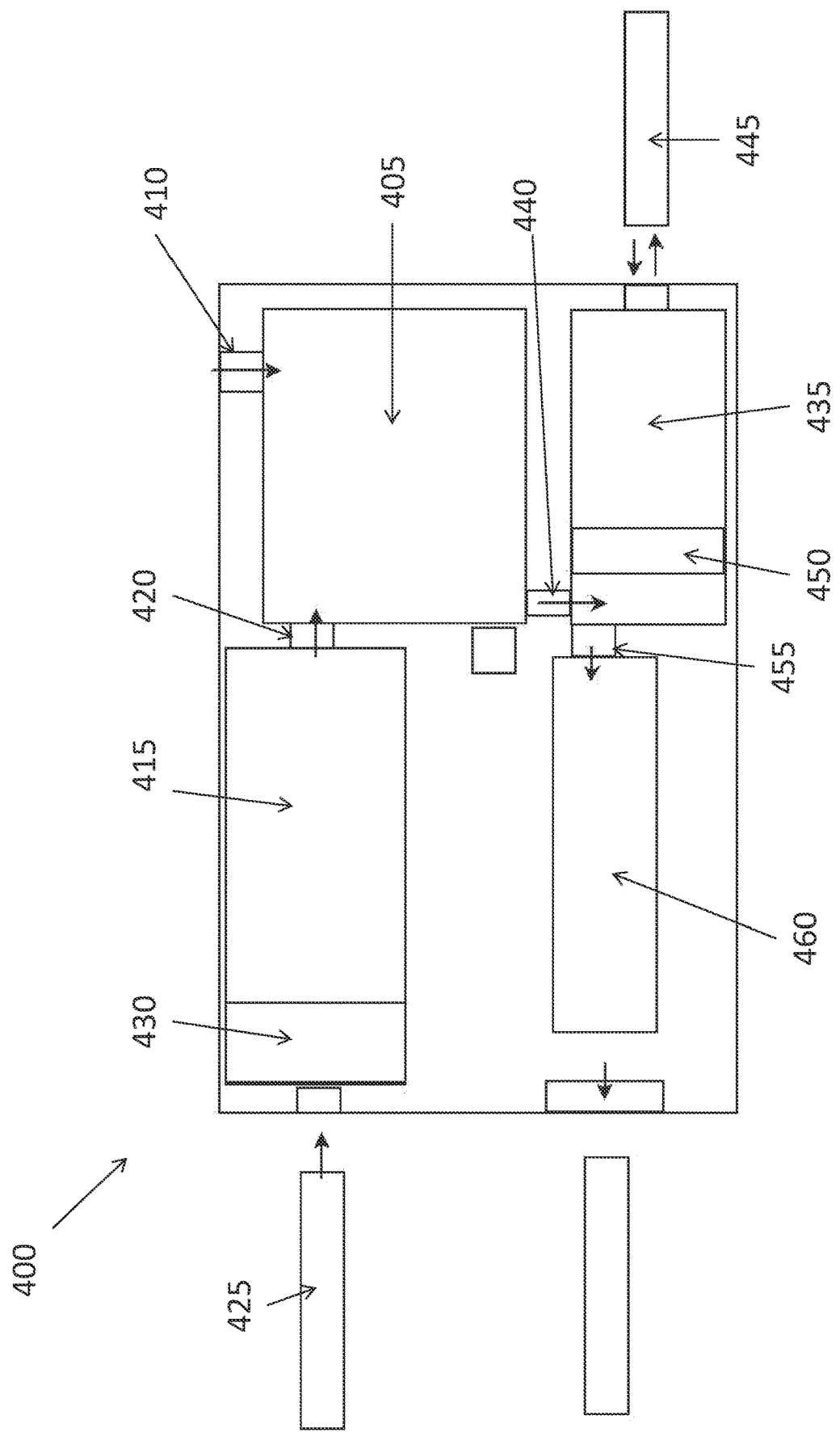
FIG. 4 depicts a first representative example of a rigid, self-contained cartridge suitable for use with the extracorporeal shockwave and/or mechanical impact devices provided by the present disclosure. In the depicted embodiment, several internal components are flexible containers.

In the embodiment depicted in FIG. 4, the stem cell containing fraction is transferred from the interior of the cell reservoir 435, through the fourth one-way valve 455 into a centrifuge tube 460 contained within the cartridge 400. The stem cell fraction is moved into the centrifuge tube 460 via use of the second external actuator 445 that moves the second plunger 450 in order to force the saline through the third one-way valve 440 and into the centrifuge tube 460. This movement can be performed manually or it can be automated, as described herein. The centrifuge tube 460 is then removed from the cartridge 400 for centrifugation. Centrifugation proceeds as described in either of the two embodiments described above; a pellet of stem cells remains at the bottom of the centrifuge tube 460.

Figure 5:
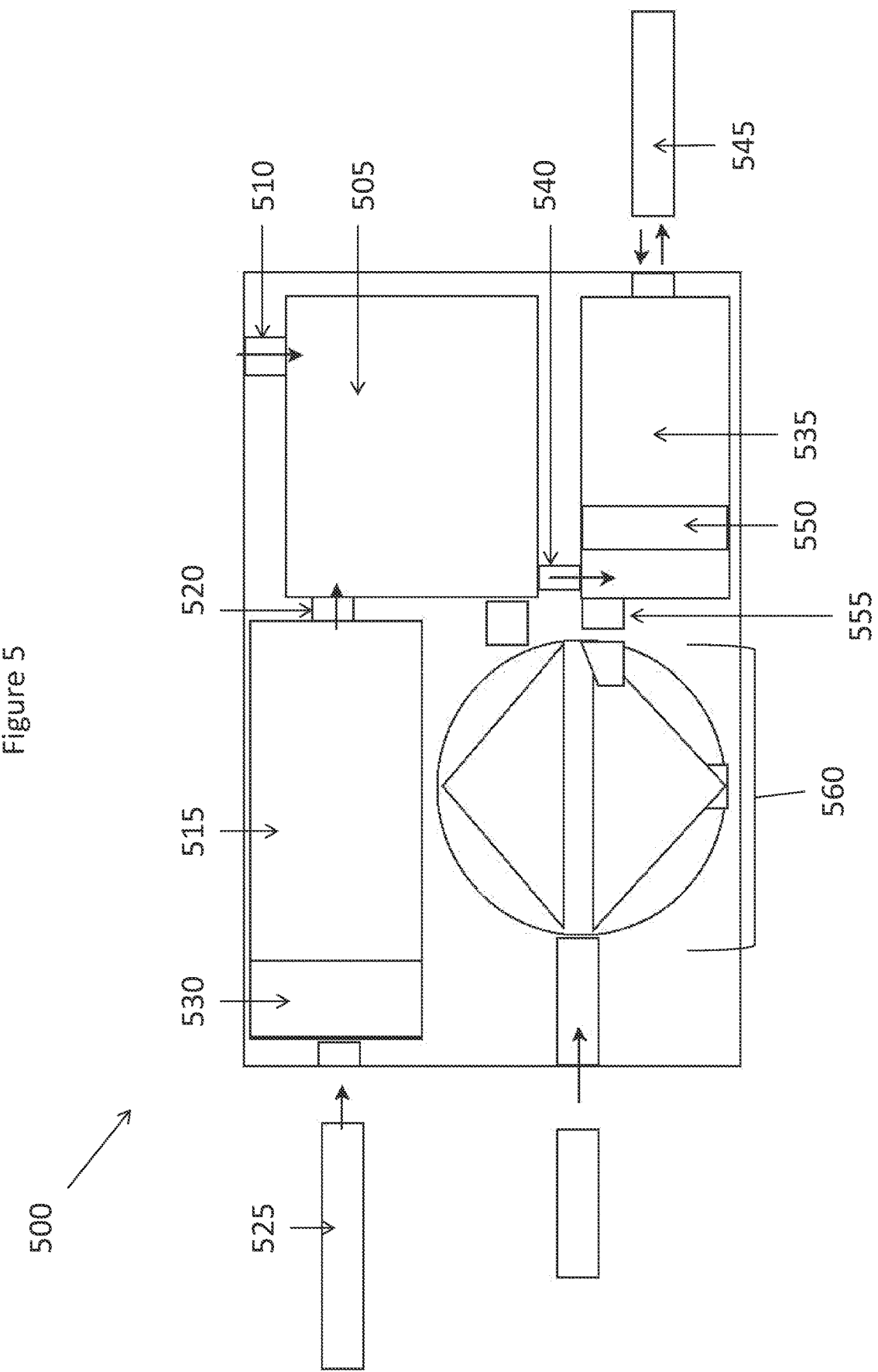
FIG. 5 depicts representative example of a rigid, self-contained cartridge suitable for use with the extracorporeal shockwave and/or mechanical impact devices provided by the present disclosure.

In the embodiment depicted in FIG. 5, the stem cell containing fraction is transferred from the interior of the cell reservoir 535, through the fourth one-way valve 555 into a centrifugation component 560 contained within the cartridge 500. The centrifugation component 560 is a triangular chamber that acts as the centrifugal component; it spins the cells out of the saline such that the cells concentrate at a single point at the outer edge of the chamber. An access port allows a user to gain access to the stem cell pellet, in order to resuspend the pellet and/or remove it from the centrifugation component 560. In some embodiments, operation of the centrifugation component 560 is automated and controlled by an external apparatus, where the external apparatus engages with the spin chamber through a motor and gear that inserts into the cartridge at the center of the chamber. In that respect, the centrifugation component 560 can be direct drive or geared. The stem cell containing layer/infranatant is loaded into the centrifugation component as described above and the other side is balanced prior to centrifugation. Once introduced into the centrifugation component, the stem cells are centrifuged at 500 g to 1600 g for 3 to 10 minutes. In some embodiments, centrifugation occurs for 10 minutes at 1200 g.

A small amount of fluid is put into the tube in order to resuspend the cells. This is typically 1 mL to 5 mL. The fluid can be saline, platelet-rich-plasma, hyaluronan, or a fixing gel, hydrogel, scaffold, or fibrin or glue, or other compound.

With the cells in suspension, they are sucked into a syringe through a hypodermic needle for further use. This is done automatically by the processing machine, or manually by an operator.

A small amount of fluid is used to resuspend the stem cells. In some embodiments, the amount of fluid added to resuspend the cells ranges from 1 mL to 5 mL. In some embodiments, the fluid is saline, platelet-rich-plasma, hyaluronan, a fixing gel, hydrogel, scaffold, fibrin, glue, or combinations of any of the foregoing. In some embodiments, the cells are resuspended in the centrifugation aspirate.

With the stem cells floating in suspension, they are ready for use. Such use can include, without limitation, reintroduction into the patient from which they were derived, cryopreservation, expansion, and the like. In some embodiments, the concentrated, resuspended stem cells are moved into a syringe, via a hypodermic needle, for patient use. In some embodiments the concentrated, resuspended stem cells are seeded into a tissue-scaffold for growing into, cardiac, muscle, bone, cartilage, liver, kidney, or other tissue and organ structures. In some embodiments the concentrated, resuspended stem cells are transformed into induced-pluripotent stem cells by causing them to express pluripotency transcription factors.

Devices

As stated above, the present disclosure provides methods and systems for bioprocessing tissue samples. In various aspects, the present disclosure also provides easy-to-use devices suitable for use with the disclosed methods, such devices being closed to the outside environment and designed for single use. Such devices include single-use cartridges that allow for complete processing within a single device.

Containers

The embodiments described above utilize one or more containers as receptacles of wither tissue samples, fat samples, fractions containing desired cellular fractions, stem cell-containing fractions, or combinations of any of the foregoing. Such containers include the container utilized in step 105 of FIG. 1; container 205; adipose chambers 405, 505; fluid reservoir 415, 515; and cell reservoir 435, 535. These containers, which are suitable for use with the systems and methods provided by the present disclosure, can be flexible, rigid or semi-rigid. In some embodiments, a container is a syringe.

Each of the containers utilized in step 105 of FIG. 1; container 205; adipose chambers 405, 505; fluid reservoir 415, 515; and cell reservoir 435, 535, is closed to the outside environment, either by itself or as part of an enclosed cartridge, and is disposable.

In some embodiments, each of the containers utilized in step 105 of FIG. 1; container 205; adipose chambers 405, 505; fluid reservoir 415, 515; and cell reservoir 435, 535 is a flexible container, for example a flexible bag. In such embodiments, each container may be made of ethylene vinyl acetate (EVA), poly(vinyl) chloride (PVC), ethylene-vinyl acetate (EVA), nylon, or other plastics.

Each of the flexible containers may be blow-molded. In some embodiments, each of the flexible containers may be radio frequency, high frequency or dielectric welded and may be blow-molded.

In some embodiments, each of the flexile containers is a three-dimensional bag having at least one outlet that is in fluid connection with the interior chamber of the flexible container. In some embodiments, a single container can have more than one outlet that is in fluid connection with the interior chamber of the container. Such outlets can be used for, for example, draining fluid from the interior chamber of the container, or moving fluid from the interior of the container to another container.

In some embodiments, a container can comprise one or more holes located on the outside of the container, along an edge, that may be used to hang the container in space.

The total volume of a container may be from 5 to 50 fluid ounces, in some embodiments from 9 to 19 fluid ounces.

In some embodiments, in order to receive input, in the form of a tissue sample, sterile saline or otherwise, a container is configured to receive an inlet line or connection at a discrete point, which connects to an inlet that is in fluid connection with the interior of the container. In order to maintain the integrity of a closed, sterile environment, the inlet line or connection comprises a female luer connection which allows the container to be connected to an external device, be that a syringe containing a tissue sample, another container from which matter is to be transferred into the container in question, or otherwise. In other embodiments, the inlet line or connection comprises a sterile dock for connection to an external device using a sterile connection device.

In several embodiments, a container may be a flat bag, having a top edge, bottom edge, and two substantially similar side edges. The bottom edge includes an outlet that is in fluid connection with the interior of the bag, for draining fluid out of the bag. The flat bag also has an inlet that allows for sterile introduction of material into the interior of the bag.

In several embodiments, the container is a three-dimensional bag that is rectangular in shape, having a top edge, bottom edge, and two substantially similar side edges. The bottom edge includes an outlet that is in fluid connection with the interior of the container, for draining fluid out of the container. The top edge includes an inlet that is in fluid connection with the interior of the container, for introduction of material into the container.

In some embodiments, a container is connected to one or more other containers via lines. The lines are tubing that may be made of poly(vinyl) chloride (PVC), ethylene-vinyl acetate (EVA), or other materials.

In some embodiments, the container may be semi rigid. In such embodiments, the container comprises a rigid plastic housing that maintains its shape and is capable of holding a flexible container inside of the housing during tissue processing. The housing is configured such that it contains a point of attachment to the platform 210 or 315.

The rigid plastic housing can be made of any suitable rigid-plastic material including, for example, high-density polyethylene (HDPE) or polypropylene (PP). The rigid plastic material exhibits no elastic deformation, nor does it display any of the elastic behavior typically displayed by flexible plastics. The rigid plastic housing may be injection molded or die-cut.

In some embodiments, a flexible container is contained within the rigid plastic housing, which may or may not completely enclose the flexible container. In some embodiments, the flexible container is not completely enclosed within the rigid plastic housing; rather, the housing partially encloses the flexible container, holding it in place during tissue processing.

Cartridges

In various aspects, cartridges suitable for use with the present disclosure are three-dimensional containers capable of housing one or more containers within their interior. The internal containers can be connected by one or more lines and/or valves. Examples of suitable cartridges are the cartridges 400, 500 depicted in FIGS. 4 and 5.

In some embodiments, the cartridges are made from a rigid plastic material that maintains its shape and is capable of holding at least one, and preferably a plurality, of flexible containers inside of the cartridges during tissue processing. The containers are configured such that they contain one or more points of attachment to the platform 210 or 315.

The rigid plastic can be made of any suitable rigid-plastic material including, for example, high-density polyethylene (HDPE) or polypropylene (PP). The rigid plastic material exhibits no elastic deformation, nor does it display any of the elastic behavior typically displayed by flexible plastics. The rigid plastic cartridges may be injection molded or die-cut.

Other aspects of the containers are described above.

Centrifuge Tubes

Centrifuge tubes suitable for use with the methods and devices of the present disclosure are precision-made, high-strength tubes of glass or plastic designed to fit exactly in a centrifuge rotor. The capacity of the centrifuge tubes can vary, depending on the total volume of the tissue sample to be processed. In some embodiments, the centrifuge tubes have a capacity ranging from 1 mL to 50 mL, in some embodiments from 0.5 mL to 20 mL, and in some embodiments from 250 µL to 2.0 mL.

In some embodiments, the centrifuge tubes are Eppendorf® tubes, in some embodiments microfuge tubes, and in some embodiments microcentrifuge tubes.

The material of the centrifuge tubes can vary. In some embodiments, the centrifuge tubes are made of glass. In some embodiments, the centrifuge tubes are plastic. In each embodiment, the centrifuge tubes are designed for single-use and are disposable. In some embodiments the centrifuge tubes are made from a flexible, transparent plastic such as polythene, are semi-conical in shape, and comprise integral, hinged sealing caps.

One-Way Valves

A one-way valve is a valve that allows fluid to flow through it in a single direction only.

In various aspects, one-way valves suitable for use with the devices and methods of the present disclosure comprise two-port valves, having two openings—one for fluid to enter, the other for fluid to leave. The one-way valves function to provide a unidirectional flow of fluid automatically and do not require any user intervention or control. In some embodiments, the one-way valves useful for the methods and devices of the present disclosure are made of a rigid plastic, such as poly(propylene).

In some embodiments, one-way valves suitable for use with the devices and methods of the present disclosure are ball check valves, in which the component that prevents backflow of fluid is a spherical ball. In some embodiments, the ball is spring-loaded to help keep the one-way valve closed.

In some embodiments, one-way valves suitable for use with the devices and methods of the present disclosure are diaphragm check valves comprising a flexing rubber diaphragm positioned to create the valve closure. In such embodiments, pressure created on the upstream side, either by user intervention or via an automated process, causes the diaphragm to open and fluid to flow through the valve. Upon cessation of the positive pressure, the diaphragm closes, terminating fluid flow.

In some embodiments, one-way valves suitable for use with the devices and methods of the present disclosure are swing check valves or tilting disc check valves. In such embodiments, a disc is the movable part of the valve used to allow fluid flow in one direction, and block fluid regress in the opposite direction.

EXAMPLES

The materials, methods, and embodiments described herein are further defined in the following Examples. Certain embodiments are also defined in the Examples herein. It should be understood that these Examples, while indicating certain embodiments, are given by way of illustration only. From the disclosure herein and these Examples, one skilled in the art can ascertain the essential characteristics of the instant disclosure, and without departing from the spirit and scope thereof, can make various changes and modifications of the invention to adapt it to various usages and conditions.

Example 1

General Protocol for ESW Tissue Processing

A lipoaspirate is obtained from a subject, the lipoaspirate being approximately 30 cc in volume. Prior to processing, the lipoaspirate is transferred to a flexible, sterile ethylene vinyl acetate (EVA), poly(vinyl) chloride (PVC), ethylene-vinyl acetate (EVA) or nylon bag having side walls approximately 0.25 inches thick. A sterile catheter bag is sufficient.

The lipoaspirate is washed using an equal volume of sterile saline introduced into the flexible bag by connecting a male luer-lock connector from a saline bag to a female luer-lock connector located on the flexible bag and manually dispensing the saline into the flexible bag. The lipoaspirate and saline wash are then mechanically agitated by gently shaking the flexible bag.

The tissue sample/saline wash mixture is allowed to settle for at least 10 minutes to allow the lipoaspirate to float to top of the saline.

The infranatant, or saline wash, is removed from the flexible bag via a drain line located at the bottom of the flexible bag. Removal can occur by connecting a syringe to the line and drawing the infranatant out of the bag, or by gravity flow.

Washing is repeated 3-4 times, leaving the sterile saline wash in the bag on the final wash.

The next step is to apply extracorporeal shockwaves to the lipoaspirate using a Masterpuls MP100 extracorporeal shockwave generator.

The generator may make contact with the wall of the flexible bag, but care should be taken to ensure that the shockwave generator does not contact the lipoaspirate itself.

If necessary, ultrasound gel may be applied to the side of the flexible bag prior to application of the shockwaves to the lipoaspirate.

Apply ESW to the lipoaspirate for 1 to 30 minutes.

Thereafter, gently agitate the flexible bag by shaking or lightly vortexing.

Allow the now processed lipoaspirate to settle, so that what remains of the fatty tissue can float to the top of the saline.

Remove the infranatant from the flexible bag by attaching a sterile syringe to the drain tube, as described above, and drawing as much of the infranatant out as possible. Do not take any of the remaining adipose tissue.

During removal, pass the infranatant through one of three nylon mesh filters having a pore size of 40 µm, 70 µm, or 100 µm.

Distribute the infranatant into one or more sterile centrifuge tubes. If an odd number of tubes is used, ensure that a balance tube, containing sterile saline, is placed in the rotor for balance.

Centrifuge at 1,200 g for 10 min.

Optional: resuspend pellet in 1 mL RBC lysis buffer and incubate in water bath at 37° C. for 10 min. Neutralize the RBC buffer.

If no RBC lysis buffer is desired, resuspend cell pellet in 1 mL sterile saline.

Count cells.

Example 2

Comparison of Lipoaspirate Processing Methods

Abstract: the purpose of the test performed for this Example was to compare the nucleated cellular yield from mesenchymal stem cells extracted from adipose tissue using collagenase digestion vs. extracorporeal shockwave (ESW) disruption.

Materials:
  1,500 mL of 1× phosphate buffered saline (PBS)
  35 mL of 1× red blood cell (RBC) lysis buffer
  200 mL of 0.1% collagenase type I
  15 mL of 10% fetal bovine serum (FBS) in Dulbecco's modified eagle medium (DMEM)

Methods:
Control

Approximately 250 mL of a lipoaspirate was transferred into a 100 mL beaker using a sterile 60 mL catheter. Care was taken to ensure that little to no excess fluid was introduced into the beaker.

The lipoaspirate was washed four times with approximately equal volumes of sterile 1×PBS. For each wash, sterile 1×PBS was added to the beaker, the two were stirred, and the mixture was allowed to settle. The infranatant was removed from the beaker by aspirating. The lipoaspirate was washed a total of four times.

After the fourth wash, the sample was allowed to settle for 10 minutes.

A sterile 10 mL serological pipette was used to transfer 45 mL of the infranatant from the fourth and final wash into 3 sterile 50 mL conical tubes through 40 µm, 70 µm and 100 µm tube sterile filters. A total of 135 mL of infranatant was transferred for use as a control.

Collagenase Digestion 200 mL of lipoaspirate was deposited into a sterile 500 mL glass bottle. 200 mL of 0.1% collagenase type I was added to the bottle. The bottle was agitated lightly by inverting it several times, to ensure that the lipoaspirate was mixed evenly with the collagenase.

The bottle was then placed into a water bath at 37° C. Every 10 minutes, the bottle was removed from the water bath and inverted several times to redistribute the lipoaspirate, which had settled. After 30 minutes of incubation, the bottle was agitated a final time and removed from the water bath.

The exterior of the bottle was sprayed with 70% ETOH and placed in a fume hood. The lipoaspirate and collagenase mixture was allowed to settle for 10 minutes.

A sterile 10 mL serological pipette was used to transfer the infranatant into 3 sterile 50 mL conical tubes through 40 μm, 70 μm and 100 μm tube sterile filters. A total of 135 mL of infranatant was transferred. The 3 tubes, including a fourth tube containing 45 mL of water for balance, were centrifuged at 1,200 g, at 37° C., for 10 minutes to obtain a collagenase-digested cell pellet.

The exterior of the 3 tubes containing the collagenase suspension were cleaned with 70% ETOH and placed into a fume hood, leaving the balance tube out. The supernatant was aspirated away, leaving a cell pellet in each tube. Using a 25 mL serological pipette, 5 mL of 10% FBS was dispensed into each tube and each tube was vortexed for 5 seconds to resuspend the pellet. FBS was used to neutralize any remaining collagenase activity.

The 3 tubes were centrifuged at 1,200 g, at 37° C., for 10 min. The exterior of the centrifuge tubes was cleaned with 70% ETOH and the tubes were placed in a fume hood. The supernatant was aspirated away, leaving the cell pellets.

ESW Processing 200 mL of lipoaspirate was transferred into a sterile 500 mL leg catheter bag using a sterile 60 mL catheter syringe, together with all of the remaining infranatant. Sterile 1×PBS was added to achieve a total fluid volume of 200 mL, the total volume being 400 mL including the lipoaspirate. Approximately 2 mL of ultrasound gel was applied to the catheter bag. Using the large tip, approximately 10,000 ESW pulses at 2 bar and 21 Hz were administered to the sample inside of the bag. The process was repeated on the other side of the bag for an additional 10,000 ESW pulses. The exterior of the catheter bag was cleaned with 70% ETOH and it was placed into a fume hood.

The bag was agitated and emptied into a 500 mL beaker and the suspension was allowed to settle for 10 minutes.

Using a sterile 10 mL serological pipette, the infranatant was transferred into 3 sterile 50 mL conical tubes through 40 μm, 70 μm and 100 μm tube sterile filters. A total of 135 mL of infranatant was transferred.

Concentration and Lysis

The 3 tubes containing the control suspension and 3 tubes containing the processed suspension were centrifuged at 1,200 g and 37° C. for 10 minutes. The supernatant was aspirated away from all tubes, leaving each pellet and 5 mL of 1×RBC lysis buffer was added to each tube. Each tube was vortexed for 5 seconds to re-suspend the pellet and the tubes were placed into a 37° C. water bath for 10 minutes.

The exterior of each tube was sanitized with 70% ETOH and the tubes were placed in a fume hood. 25 mL of sterile 1×PBS was added to each tube to dilute and neutralize the lysis buffer.

Cell Counting

Using sterile micropipette tips, 300 μL of sterile 1×PBS was transferred into 6 sterile 0.5 mL microcentrifuge tubes. 75 μL of each 50 mL sample tube was also transferred into each microcentrifuge tube for cell counting.

The number of cells in each sample was counted using a MoxiZ cell counter with both M type and S type cassettes. For counting, 100 μL of trypan blue was added to each microcentrifuge tube, 10 μL of each sample was loaded into a hemocytometer well and the cells were counted.

Results:

MoxiZ Cell Counter

Table 1 shows the results of the cell counts using the MoxiZ automated cell counter. Two types of cassettes were used for counting, M and S. In the Sample column, 'c' signifies collagenase digestion, 'e' for ESW processing and '0' for control. Only counts with 'y' in the 'Complete' column are valid.

TABLE 1

| Test Number | Sample | Filter Size (μL) | Cassette | Complete | Count (cells/mL) | Average Cell Size (μm) | Average Cell Volume (pL) |
|---|---|---|---|---|---|---|---|
| 377 | 0 | 100 | m | y | 2.42E+05 | 6.082 | 0.118 |
| 373 | 0 | 40 | m | y | 2.11E+05 | 6.021 | 0.114 |
| 375 | 0 | 70 | m | y | 2.14E+05 | 6.087 | 0.118 |
| 387 | e | 100 | s | y | 2.22E+05 | 5.937 | 0.11 |
| 379 | e | 40 | m | y | 1.72E+05 | 6.196 | 0.125 |
| 381 | e | 70 | m | y | 2.08E+05 | 6.255 | 0.128 |
| 380 | e | 70 | m | y | 2.01E+05 | 6.633 | 0.153 |
| 376 | 0 | 100 | m | n | 1.42E+08 | 10.168 | 0.55 |
| 389 | 0 | 100 | s | n | 1.19E+06 | 7.952 | 0.263 |
| 372 | 0 | 40 | m | n | 2.05E+06 | 9.158 | 0.402 |
| 386 | 0 | 40 | s | n | 1.77E+06 | 9.259 | 0.416 |
| 374 | 0 | 70 | m | n | 5.00E+07 | 8.263 | 0.295 |
| 388 | 0 | 70 | s | n | 7.67E+05 | 10.351 | 0.581 |
| 382 | e | 100 | m | n | 1.27E+06 | 8.77 | 3.53 |
| 383 | e | 100 | m | n | 8.51E+05 | 7.615 | 0.231 |
| 378 | e | 40 | m | n | 1.80E+06 | 10.173 | 0.551 |
| 384 | e | 40 | s | n | 1.66E+06 | 8.448 | 0.316 |
| 385 | e | 70 | s | n | 9.04E+05 | 9.531 | 0.453 |
|  | c | 100 | m | y | 4.32E+05 | 7.159 | 0.192 |
|  | c | 100 | s | y | 3.12E+05 | 6.773 | 0.163 |
|  | c | 40 | m | y | 4.07E+05 | 7.345 | 0.207 |
|  | 0 | 40 | s | n | 1.81E+06 | 11.119 | 0.72 |
|  | 0 | 40 | m | n | 1.20E+06 | 6.978 | 0.178 |
|  | 0 | 70 | m | n | 2.33E+06 | 7.394 | 0.212 |
|  | 0 | 70 | m | n | 7.36E+05 | 6.279 | 0.13 |
|  | c | 70 | m | n | 5.55E+06 | 9.401 | 0.435 |
|  | c | 70 | s | n | 2.02E+06 | 9.897 | 0.508 |
| 424 | 0 | 100 | s | y | 5.40E+05 | 6.376 | 0.136 |
| 416 | 0 | 100 | m | y | 1.34E+05 | 6.524 | 0.145 |
| 415 | 0 | 40 | m | y | 1.25E+05 | 6.322 | 0.132 |
| 413 | 0 | 70 | m | y | 1.41E+05 | 6.233 | 0.127 |
| 420 | e | 100 | m | y | 2.46E+05 | 6.867 | 0.17 |

TABLE 1-continued

| Test Number | Sample | Filter Size (μL) | Cassette | Complete | Count (cells/mL) | Average Cell Size (μm) | Average Cell Volume (pL) |
|---|---|---|---|---|---|---|---|
| 417 | e | 40 | m | y | 1.67E+05 | 6.407 | 0.138 |
| 418 | e | 70 | m | y | 2.18E+05 | 6.27 | 0.129 |
| 416 | 0 | 100 | m | n | 1.51E+07 | 11.459 | 0.788 |
| 414 | 0 | 100 | m | n | 7.34E+05 | 6.493 | 0.143 |
| 412 | 0 | 40 | m | n | 7.64E+06 | 8.292 | 0.299 |
| 421 | 0 | 40 | s | n | 2.53E+06 | 9.511 | 0.451 |
| 422 | 0 | 40 | s | n | 1.75E+06 | 10.231 | 0.561 |
| 423 | 0 | 70 | s | n | 2.06E+06 | 11.347 | 0.765 |
| 419 | e | 100 | m | n | 4.50E+06 | 11.626 | 0.823 |
| 428 | e | 100 | s | n | 3.11E+06 | 8.158 | 0.284 |
| 426 | e | 40 | s | n | 1.24E+06 | 10.186 | 0.553 |
| 425 | e | 40 | s | n | 7.99E+05 | 10.188 | 0.554 |
| 427 | e | 70 | s | n | 5.49E+05 | 8.768 | 0.353 |
|  | c | 100 | s | y | 4.32E+05 | 6.283 | 0.13 |
|  | c | 100 | m | y | 3.93E+05 | 6.972 | 0.177 |
|  | c | 70 | m | y | 3.11E+05 | 7.006 | 0.18 |
|  | 0 | 100 | m | n | 7.89E+08 | 8.455 | 0.443 |
|  | 0 | 100 | s | n | 1.92E+06 | 10.829 | 0.665 |
|  | 0 | 40 | m | n | 2.70E+07 | 9.092 | 0.393 |
|  | 0 | 40 | s | n | 7.21E+05 | 6.876 | 0.17 |
|  | 0 | 70 | m | n | 3.57E+06 | 10.556 | 0.616 |
|  | 0 | 70 | s | n | 1.38E+06 | 10.327 | 0.577 |
|  | c | 40 | m | n | 5.22E+06 | 8.805 | 0.357 |
|  | c | 40 | s | n | 1.27E+06 | 7.043 | 0.183 |
|  | c | 70 | s | n | 1.29E+06 | 6.458 | 0.141 |
|  | 0 | 100 | s | y | 2.15E+05 | 5.909 | 0.108 |
|  | 0 | 40 | m | y | 1.95E+05 | 6.888 | 0.171 |
|  | e | 100 | m | y | 6.97E+05 | 6.669 | 0.155 |
|  | e | 40 | m | y | 7.08E+05 | 6.853 | 0.169 |
|  | 0 | 100 | m | n | 8.20E+05 | 6.897 | 0.172 |
|  | 0 | 40 | s | n | 2.32E+06 | 10.365 | 0.583 |
|  | 0 | 70 | m | n | 3.19E+06 | 10.4 | 0.589 |
|  | 0 | 70 | s | n | 1.98E+06 | 9.702 | 0.478 |
|  | e | 100 | s | n | 1.60E+06 | 5.837 | 0.104 |
|  | e | 40 | s | n | 1.48E+06 | 6.078 | 0.118 |
|  | e | 70 | m | n | 4.01E+06 | 8.499 | 0.321 |
|  | e | 70 | s | n | 2.02E+06 | 7.934 | 0.261 |

Hemocytometer

Table 2 details the counts obtained from the visual hemocytometer, with cell counts from each quadrant, the sum of the quadrants, the dilution factor, and the total calculated cells. The number of cells should be taken in reference to the count of the cells in the control population. The ratio of processed cells vs. control cells is a key indicator of yield.

TABLE 2

| Sample | Filter Size (μL) | Quadrant 1 | Quadrant 2 | Quadrant 3 | Quadrant 4 | Quad Sum | Dilution (μL) | Suspension (μL) | Factor | Total | Ratio |
|---|---|---|---|---|---|---|---|---|---|---|---|
| 0 | 100 | 4 | 5 | 4 | 4 | 17 | 300 | 75 | 4 | 680000 |  |
| 0 | 40 | 0 | 0 | 1 | 2 | 3 | 300 | 75 | 4 | 120000 |  |
| 0 | 70 | 0 | 0 | 0 | 0 | 0 | 300 | 75 | 4 | 0 |  |
| E | 100 | 8 | 5 | 11 | 9 | 33 | 300 | 75 | 4 | 1320000 | 1.94 |
| E | 40 | 3 | 1 | 2 | 3 | 9 | 300 | 75 | 4 | 360000 | 3.00 |
| E | 70 | 2 | 1 | 2 | 3 | 8 | 300 | 75 | 4 | 320000 | #DIV/0! |
| 0 | 100 | 10 | 11 | 10 | 13 | 44 | 300 | 75 | 4 | 1760000 |  |
| 0 | 40 | 18 | 13 | 12 | 12 | 55 | 300 | 75 | 4 | 2200000 |  |
| 0 | 70 | 10 | 14 | 1 | 9 | 34 | 300 | 75 | 4 | 1360000 |  |
| C | 100 | 27 | 36 | 35 | 27 | 125 | 300 | 75 | 4 | 5000000 | 2.84 |
| C | 40 | 13 | 16 | 19 | 23 | 71 | 300 | 75 | 4 | 2840000 | 1.29 |
| C | 70 | 15 | 22 | 22 | 31 | 90 | 300 | 75 | 4 | 3600000 | 2.65 |
| 0 | 100 | 3 | 1 | 2 | 0 | 6 | 300 | 75 | 4 | 240000 |  |
| 0 | 40 | 2 | 3 | 4 | 2 | 11 | 300 | 75 | 4 | 440000 |  |
| 0 | 70 | 2 | 4 | 2 | 1 | 9 | 300 | 75 | 4 | 360000 |  |
| E | 100 | 20 | 6 | 16 | 12 | 54 | 300 | 75 | 4 | 2160000 | 9.00 |
| E | 40 | 19 | 22 | 28 | 24 | 93 | 300 | 75 | 4 | 3720000 | 8.45 |
| E | 70 | 3 | 4 | 5 | 4 | 16 | 300 | 75 | 4 | 640000 | 1.78 |

Summary

Of the valid counts using the MoxiZ automated cell counter, the aggregated averages for cell counts for control, collagenase, and ESW are as shown in Table 3:

TABLE 3

| Sample | Average | SD |
| --- | --- | --- |
| 0 | 2.24E+05 | 1.18E+05 |
| C | 3.81E+05 | 5.11E+04 |
| E | 3.15E+05 | 2.08E+05 |

Collagenase consistently produced about 3.8E+05 cells/mL. ESW ranged from 1.67e+05 to 7.08e+05 cells/mL.

Looking at the ratios of cells in the hemocytometer counts, the ESW process produced the highest ratios with ratios ranging from 1.78 to 9.0 times higher than control. Collagenase only produced ratios ranging from 1.29 to 2.84 times higher than control.

DISCUSSION

These data indicate that ESW is effective to produce high numbers of mesenchymal stem cells from adipose tissue. Based on these data, it is concluded that ESW is a viable alternative to either ultrasound or collagenase processing of adipose tissue to obtain mesenchymal stem cells. In comparing peaks, ESW produced cellular yields of 7.08e+05 compared to the collagenase peak of 4.32e+05—an increase in yield of 164%.

Given the data presented above, it is reasonable to conclude that a 50 cc to 60 cc sample of lipoaspirate would yield about 5 million cells from ESW processing and about 3 million cells from collagenase digestion.

It is therefore apparent that use of ESW to liberate stem cells from adipose tissue confers a significant advantage over known techniques.

What is claimed is:

1. A method of isolating a stromal vascular fraction from tissue, comprising:
   placing a tissue sample into a processing container of a tissue processing device;
   subjecting the tissue sample to force from mechanical impacts to break down the tissue; and
   separating the stromal vascular fraction from the tissue; wherein:
   the mechanical impacts are generated by an impact arm that makes physical contact with the processing container; and
   the impact arm does not physically contact the tissue.

2. The method of claim 1, wherein the processing device comprises:
   a platform to which the processing container is secured; and
   a first motor that drives up and down articulation of the impact arm.

3. The method of claim 1, wherein the processing container is a cartridge.

4. The method of claim 1, wherein the force from the mechanical impacts is delivered to the tissue through a wall of the processing container.

5. The method of claim 1, wherein the separating comprises allowing the tissue to separate from an aqueous layer, the aqueous layer comprising the stromal vascular fraction.

6. The method of claim 1, wherein the stromal vascular fraction is isolated from the tissue in 30 minutes or less.

7. The method of claim 1, wherein the stromal vascular fraction comprises stem cells, growth factors and progenitor cells.

8. The method of claim 1, wherein the tissue is selected from adipose tissue, brain tissue, pharyngeal tissue, laryngeal tissue, heart tissue, arterial tissue, muscle tissue, liver tissue, gall bladder tissue, kidney tissue, small intestinal tissue, large intestinal tissue, lymph node tissue, lung tissue, spleen tissue, bone marrow tissue, stomach tissue, venous tissue, pancreatic tissue, urinary bladder tissue, bone, teeth, dentin tissue, gum tissue, skin tissue, pineal gland tissue, pituitary gland tissue, thyroid gland tissue, adrenal gland tissue, pancreatic tissue, ovarian tissue and testicular tissue.

9. The method of claim 2, wherein the first motor is a variable speed motor.

10. The method of claim 9, wherein the first motor drives the impact arm such that the impact arm articulates up and down at a rate of up to 30,000 rpm, making physical contact with the processing container.

11. The method of claim 10, wherein the first motor drives the up and down articulation of the impact arm at a rate of up to 5,000 rpm.

12. The method of claim 10, wherein the articulation of the impact arm generates mechanical impacts that are imparted to an outside surface of the processing container that break down the tissue and separate the stromal vascular fraction from the adipose tissue.

13. The method of claim 12, wherein the first motor controls the speed at which the impact arm makes contact with the processing container.

14. The method of claim 13, wherein the first motor is controlled by a microprocessor.

15. The method of claim 1, wherein the processing container is a cartridge.

16. The method of claim 1, wherein the processing container does not contain enzymes other than those in the tissue.

17. The method of claim 1, wherein the impacts do not cause mixing of the stromal vascular fraction and the remaining tissue.

18. The method of claim 2, wherein the processing device comprises a second motor that controls movement of the platform.

19. The method of claim 18, wherein the second motor controls vertical movement of the platform.

20. The method of claim 4, wherein the mechanical impacts are imparted to an outside surface of the processing container.

* * * * *